(12) United States Patent
Voldman et al.

(10) Patent No.: US 10,098,581 B2
(45) Date of Patent: Oct. 16, 2018

(54) INTEGRATED ELECTRICAL PROFILING SYSTEM FOR MEASURING LEUKOCYTES ACTIVATION FROM WHOLE BLOOD

(71) Applicant: Massachusetts Institute of Technology, Cambridge, MA (US)

(72) Inventors: Joel Voldman, Belmont, MA (US); Hao-Wei Su, Cambridge, MA (US); Javier Lopez Prieto, Emeryville, CA (US); Jongyoon Han, Bedford, MA (US); Lidan Wu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 298 days.

(21) Appl. No.: 15/111,584

(22) PCT Filed: Jan. 16, 2015

(86) PCT No.: PCT/US2015/011801
§ 371 (c)(1),
(2) Date: Jul. 14, 2016

(87) PCT Pub. No.: WO2015/156876
PCT Pub. Date: Oct. 15, 2015

(65) Prior Publication Data
US 2016/0331297 A1    Nov. 17, 2016

Related U.S. Application Data

(60) Provisional application No. 61/928,933, filed on Jan. 17, 2014.

(51) Int. Cl.
*G01N 15/10*    (2006.01)
*G01N 15/14*    (2006.01)
(Continued)

(52) U.S. Cl.
CPC ............ *A61B 5/412* (2013.01); *A61B 5/1468* (2013.01); *A61B 5/1486* (2013.01);
(Continued)

(58) Field of Classification Search
CPC ....... A61B 5/41; A61B 5/412; A61B 5/14546; A61B 5/145; A61B 5/1468;
(Continued)

(56) References Cited

U.S. PATENT DOCUMENTS

2005/0175981 A1 *    8/2005    Voldman ................. B03C 5/005
                                                        435/4
2006/0171855 A1      8/2006    Yin et al.
(Continued)

FOREIGN PATENT DOCUMENTS

WO    WO 2011/109762 A1    9/2011
WO    WO 2014/046621 A1    3/2014

OTHER PUBLICATIONS

Cohen, J. "The Immunopathogenesis of Sepsis," *Nature*, 420(6917): 885-891 (Dec. 19-26, 2002).
(Continued)

*Primary Examiner* — Susan D Leong
(74) *Attorney, Agent, or Firm* — Hamilton, Brook, Smith & Reynolds, P.C.

(57) ABSTRACT

A system includes a microfluidic device configured to isolate one or more particles from a mixture, a flow rate matching device configured to match flow rate of the microfluidic device with flow rate of an electrical measurement device configured to measure an electrical property of the isolated particles, and an electrical measurement device configured to measure an electrical property of the isolated particles.

22 Claims, 24 Drawing Sheets

(51) Int. Cl.
*G01N 15/00* (2006.01)
*G01N 15/02* (2006.01)
*A61B 5/00* (2006.01)
*A61B 5/145* (2006.01)
*A61B 5/1468* (2006.01)
*A61B 5/1486* (2006.01)
*B01L 3/00* (2006.01)
*G01N 33/487* (2006.01)

(52) U.S. Cl.
CPC .... *A61B 5/14546* (2013.01); *B01L 3/502715* (2013.01); *B01L 3/502746* (2013.01); *B01L 3/502753* (2013.01); *B01L 3/502761* (2013.01); *G01N 15/1031* (2013.01); *G01N 15/1404* (2013.01); *G01N 15/1459* (2013.01); *G01N 15/1463* (2013.01); *G01N 15/1484* (2013.01); *G01N 33/48735* (2013.01); *B01L 2200/0605* (2013.01); *B01L 2200/0647* (2013.01); *B01L 2200/0652* (2013.01); *B01L 2300/0645* (2013.01); *B01L 2300/088* (2013.01); *B01L 2300/0816* (2013.01); *G01N 2015/008* (2013.01); *G01N 2015/0073* (2013.01); *G01N 2015/1006* (2013.01); *G01N 2015/149* (2013.01); *G01N 2015/1486* (2013.01); *G01N 2800/7095* (2013.01)

(58) Field of Classification Search
CPC ............... G01N 15/1031; G01N 15/02; G01N 15/0266; G01N 15/0288; G01N 15/0294; G01N 15/10; G01N 15/1025; G01N 15/1056; G01N 15/1075; G01N 15/1081; G01N 15/1087; G01N 15/1093; G01N 15/14; G01N 15/1404; G01N 15/1484; G01N 15/1463; G01N 15/1459; G01N 2015/1025; G01N 2015/1031; G01N 2015/1043; G01N 2015/1056; G01N 2015/1486; G01N 2015/149; B01L 2200/0605; B01L 2200/0647; B01L 2200/0652; B01L 2200/0636; B01L 2200/0663; B01L 2300/0627; B01L 2300/0636; B01L 2300/0663; B01L 2300/0816
See application file for complete search history.

(56) References Cited

U.S. PATENT DOCUMENTS

| 2008/0135502 | A1 | 6/2008 | Pyo et al. |
| 2008/0261258 | A1 | 10/2008 | Smith et al. |
| 2009/0294291 | A1 | 12/2009 | Voldman et al. |
| 2010/0098585 | A1* | 4/2010 | Chiu ................ B01L 3/502707 422/68.1 |
| 2011/0053289 | A1 | 3/2011 | Lowe et al. |
| 2011/0070581 | A1 | 3/2011 | Gupta et al. |
| 2012/0140205 | A1* | 6/2012 | Kaduchak .......... G01N 15/1404 356/39 |
| 2012/0142032 | A1 | 6/2012 | Morgan et al. |
| 2013/0130226 | A1 | 5/2013 | Lim et al. |
| 2013/0171628 | A1 | 7/2013 | Di Carlo et al. |

OTHER PUBLICATIONS

International Preliminary Report on Patentability dated Jul. 19, 2016 for International Application No. PCT/US2015/011801, entitled "Integrated Electrical Profiling System for Measuring Leukocytes Activation From Whole Blood".

International Search Report and Written Opinion dated Sep. 30, 2015 for International Application No. PCT/US2015/011801 entitled "Integrated Electrical Profiling System for Measuring Leukocytes Activation From Whole Blood".

Lenshof, A. et al., "Acoustofluidics 5: Building microfluidic acoustic resonators", *Lab on a Chip*, 12(4): 684-95 (Feb. 21, 2012).

Nikolic-Jaric, M. et al., "Electronic Detection of Dielectrophoretics Forces Exerted on Particles Flowing Over Interdigitated Electrodes", *Biomicrofluidics*, 6(2): 024117-024117-15 (2012).

Su, H-W., et al., "Integrated system for electrical characterization of leukocytes from diluted whole blood", Poster Presented at SLAS (2014).

Vahey, M. D. and Voldman, J., "An Equilibrium Method for Continuous-Flow Cell Sorting Using Dielectrophoresis," *Analytical Chemistry*, 80: 3135-3143 (2008).

Vahey, M. D., and Voldman, J., "High-Throughput Cell and Particle Characterization Using Isodielectric Separation," *Analytical Chemistry*, 81(7): 2446-2455 (2009).

Valero, A. et al., "A Miniaturized Continuous Dielectrophoretic Cell Sorter and Its Applications," *Biomicrofluidics*, 4(2): 022807 (2010).

Wu, L. et al., "Separation of Leukocytes from Blood Using Spiral Channel with Trapezoid Cross-Section," *Analytical Chemistry*, 84(21): 9324-9331 (Nov. 2012).

* cited by examiner a)

b)

c) QUADRUPOLE CONFIGURATION

INTEGRATED ELECTRICAL PROFILING SYSTEM FOR MEASURING LEUKOCYTES ACTIVATION FROM WHOLE BLOOD

RELATED APPLICATION

This application is the U.S. National Stage of International Application No. PCT/US2015/011801, filed Jan. 16, 2015, which designates the U.S., published in English, and claims the benefit of U.S. Provisional Application No. 61/928,933, filed on Jan. 17, 2014. The entire teachings of the above applications are incorporated herein by reference.

GOVERNMENT SUPPORT

This invention was made with government support under N66001-11-1-4182 from DARPA. The government has certain rights in the invention.

BACKGROUND OF THE INVENTION

Sepsis is an uncontrolled activation of the immune system that causes an excessive inflammatory response. There is an unmet need to develop tools to monitor sepsis progression, which occurs quickly and provides few clues to indicate if treatment is effective. One molecular aspect of sepsis progression is leukocyte activation, which plays an important role in the immune response. Surface markers and cytokines are existing measures of leukocyte activation, however the time needed to assay them precludes their use in real time.

Therefore, there is a need for systems and methods to address the above mentioned problems.

SUMMARY OF THE INVENTION

The invention is generally directed to systems and methods of measuring electrical properties of particles isolated from a mixture.

In one embodiment, a system includes a microfluidic device configured to isolate one or more particles from a mixture, a flow rate matching device configured to match flow rate of the microfluidic device with flow rate of an electrical measurement device configured to measure an electrical property of the isolated particles, and an electrical measurement device configured to measure an electrical property of the isolated particles.

In another embodiment, a method of detecting an inflammatory condition in an individual in need thereof includes introducing a sample from the individual comprising one or more white blood cells into a system, wherein the system comprises a microfluidic device that isolates the one or more white blood cells from the sample, an iso-dielectric separation (IDS) device that measures the iso-dielectric point of a cell (IDS device), and a reservoir configured to match flow rate from the microfluidic device to the flow rate of the IDS device, wherein the white blood cells are isolated from the sample in the microfluidic device, then introduced into the reservoir and maintained in the reservoir under conditions in which the flow rate of the one or more isolated white blood cells is matched to the flow rate of the IDS device, then introduced into the IDS device and maintained under conditions in which the iso-dielectric point (IDP) of the white blood cells is measured, and wherein a greater number of cells in the sample having a shift in IDP compared to a control indicates an inflammatory condition.

In yet another embodiment, a method of detecting leukocyte activation includes introducing a sample comprising leukocytes into a system, wherein the system comprises a microfluidic device that isolates one or more leukocytes from the sample, an iso-dielectric separation (IDS) device that measures the iso-dielectric point of a leukocyte, and a reservoir configured to match flow rate from the microfluidic device to the flow rate of the IDS device, wherein the leukocytes are isolated from the sample in the microfluidic device, then introduced into the reservoir and maintained in the reservoir under conditions in which the flow rate of the one or more isolated leukocytes is matched to the flow rate of the IDS device, then introduced into the IDS device and maintained under conditions in which the iso-dielectric point (IDP) of the leukocytes is measured, wherein a shift in IDP of the leukocytes compared to a control indicates leukocyte activation.

This invention has many advantages, including enabling the measurement of the activation state of leukocytes from a drop of whole blood within about 15 minutes, to monitor progression of an inflammatory disease, such as sepsis, with fine temporal resolution.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A is a top view of the microfluidic device; FIG. 1B is an inset perspective view of the microchannels of the microfluidic device; FIG. 1C is a cross-sectional view of the inlet of the microfluidic device; and FIG. 1D is a cross-sectional view of the outlet of the microfluidic device.

FIG. 4b) shows cells escaping the DEP barrier at their isodielectric position (IDP) resulting in a transversal distribution of cells. FIG. 4c) shows a CCD camera used to capture video near the end of the channel. Finally image processing and cell counting quantify the IDP distribution.

FIG. 6D shows a range of frequencies in MHz (vertical axis) versus isodielectric point (IDP) measurements (pixels); FIG. 6E shows arbitrary units (vertical axis) versus IDP (horizontal axis, in pixels) at 1 MHz; and FIG. 6F shows arbitrary units (vertical axis) versus IDP (horizontal axis, in pixies) at 5 MHz.

FIG. 11(b): % activated granulocytes in IDS as a function of % activated granulocytes in flow cytometry.

FIG. 14A is a Receiver Operating Characteristic (ROC) curve for the 1 MHz IDP measurements of FIG. 6E, while

FIG. 15A is a Receiver Operating Characteristic (ROC) curve for multiple frequencies of IDP measurements, while

In FIGS. 17A and 17C, IDP in pixels is shown, versus arbitrary units, for high conductivity, medium conductivity and low conductivity media in the IDS separator, at each of the two frequencies.

In FIGS. 17B and 17D, the normalized cell counts are shown for each of the high conductivity, medium conductivity and low conductivity media.

DETAILED DESCRIPTION OF THE INVENTION

A description of example embodiments of the invention follows.

In one embodiment, a system includes a microfluidic device configured to isolate one or more particles from a mixture, a flow rate matching device configured to match the flow rate of the microfluidic device with the flow rate of an electrical measurement device configured to measure an electrical property of the isolated particles, and an electrical measurement device configured to measure an electrical property of the isolated particles.

Particles present in a variety of mixtures can be introduced into the microfluidic device. Examples of mixtures include biological fluids (e.g., a biological sample such as blood, lymph, cerebrospinal fluid, urine, and the like), liquids (e.g., water) culture media, emulsions, etc. The sample can be a fresh sample or a stored sample (e.g., frozen). A variety of particles can be separated using the microfluidic device. In a particular aspect, larger particles can be separated from smaller particles. In one aspect, larger particles can have a diameter from about 18 μm to about 50 μm and smaller particles can have a diameter from about 2 μm to about 14 μm. In some aspects, the particles can be beads. In other aspects, the particles can be cells, such as blood cells. In a particular aspect, the cells are present in a blood sample, wherein the larger cells are leukocytes (diameters in a range of between about 10 μm and about 15 μm) and the smaller cells are red blood cells (RBCs) (diameters of about 7-8 μm). In a specific aspect, the leukocytes can be neutrophils.

Any microfluidic device that can isolate one or more particles from a mixture is suitable. In a particular aspect, the microfluidic device can include at least one spiral channel having a length and a cross-section consisting of a height and a width defining an aspect ratio (i.e., aspect ratio=height/width) adapted to isolate particles along portions of the cross-section of the channel based on particle size. See PCT Application No. PCT/US2011/027276 filed on Mar. 4, 2011 and published as WO 2011/109762 A1 on Sep. 9, 2011, which is hereby incorporated by reference in its entirety. The aspect ratio of the channel can be in a range of between about 2 and about 10.

Figure 1B:
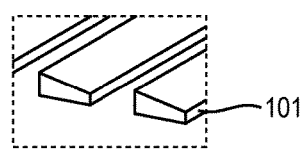
FIGS. 1A-1D are illustrations of a microfluidic device configured to isolate particles from a mixture.
Figure 1C:
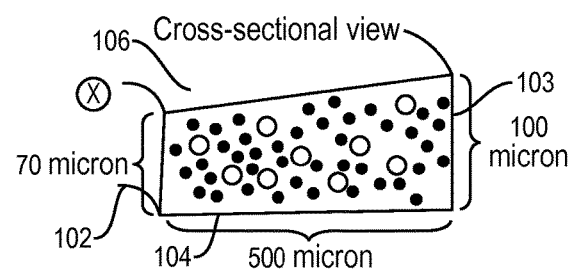
Figure 1A:
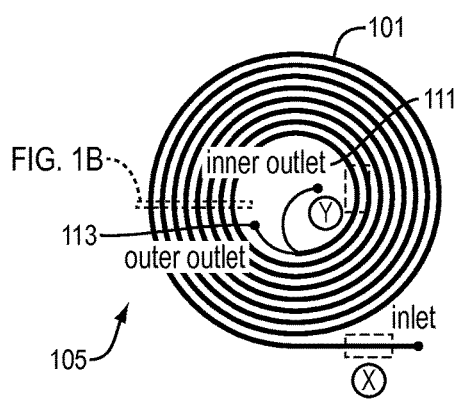
Figure 1D:
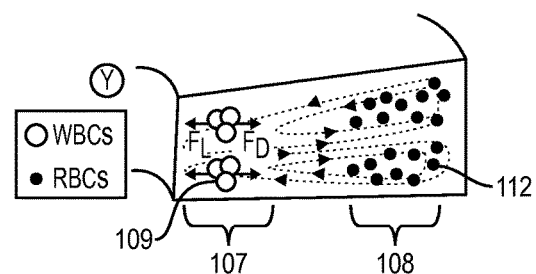

FIGS. 1A-1D are illustrations of a microfluidic device 105 configured to isolate particles from a mixture. FIG. 1A is a top view of the microfluidic device 105; FIG. 1B is an inset perspective view of the microchannels 101 of the microfluidic device 105; FIG. 1C is a cross-sectional view of the inlet of the microfluidic device 105; and FIG. 1D is a cross-sectional view of the outlet of the microfluidic device 105. In a particular aspect, the microfluidic device 105 can include a curvilinear microchannel 101 having a trapezoidal cross section defined by a radially inner side 102, a radially outer side 103, a bottom side 104, and a top side 106, the cross section having the height of the radially inner side 102 smaller than the height of the radially outer side 103, at a flow rate that isolates particles along portions 107, 108 of the cross-section of the microchannel 101 based on particle size, wherein larger particles 109 flow along the radially inner side 102 of the microchannel 101 to a first outlet 111 and smaller particles 112 flow along other portions of the microchannel 101 to at least one other outlet 113, thereby size separating the particles from the mixture. See PCT Application No. PCT/SG2013/000412 filed on Sep. 20, 2013, which is hereby incorporated by reference in its entirety. In a specific aspect, shown in FIGS. 1A-1D, the radially inner side 102 can be about 70 μm, the radially outer side 103 can be about 100 μm, and the top 106 and bottom 104 sides can be about 500 μm.

The flow rate through the microfluidic device can be in a range of between about 500 μl/min and about 2 ml/min, such as between about 500 μl/min and about 1 ml/min, between about 750 μl/min and about 1.5 ml/min, between about 1 ml/min and about 1.5 ml/min, or between about 500 μl/min and about 0.75 ml/min. In a particular aspect, the flow rate through the microfluidic device can be about 0.8 mL/min.

A variety of electrical properties of particles can be measured. Examples include electrical conductivity, electrical impedance, membrane permittivity, and cytoplasm conductivity. A variety of electrical measurement devices configured to measure the electrical properties of the isolated particles can be used. Examples include an impedance based electrical properties measurement device (see U.S. application Ser. No. 13/375,904 of H. Morgan et al., published as US 2012/0142032 A1 on Jun. 7, 2012), a multiple frequency dielectrophoresis device (see Ana Valero, Thomas Braschler, Nicolas Demierre, and Philippe Renaud, *A miniaturized continuous dielectrophoretic cell sorter and its applications*, Biomicrofluidics, vol. 4(2): 022807 (2010)), and a differential electronic detector of dielectrophoresis translation (see Marija Nikolic-Jaric, Sean F. Romanuik, Graham A. Ferrier, Tim Cabel, Elham Salimi, David B. Levin, Greg E. Bridges, and Douglas J. Thomson, *Electronic detection of dielectrophoretic forces exerted on particles flowing over interdigitated electrodes*, Biomicrofluidics. vol. 6(2): 024117-024117-15 (2012)).

In a particular aspect, the electrical measurement device configured to measure the electrical properties of the isolated particles is an iso-dielectric separation (IDS) device. See M. D. Vahey and J. Voldman, *An Equilibrium Method for Continuous-Flow Cell Sorting Using Dielectrophoresis*, Anal. Chem. vol. 80, pp. 3135-3143 (2008), which is hereby incorporated by reference in its entirety. The IDS device can be single-sided or double-sided. For the single-sided IDS device, the flowrate can be in a range of between about 0.5 μl/min and about 2 μl/min, such as between about 1.0 μl/min and about 2 μl/min, between about 0.5 μl/min and about 1.5 μl/min, between about 1.0 μl/min and about 1.5 μl/min, or between about 1.5 μl/min and about 2 μl/min. For the double-sided IDS device, the flowrate can be in a range of between about 0.25 μl/min and about 1 μl/min, such as between about 0.25 μl/min and about 0.5 μl/min, between about 0.5 μl/min and about 1 μl/min, or between about 0.25 μl/min and about 0.5 μl/min.

Figure 2:
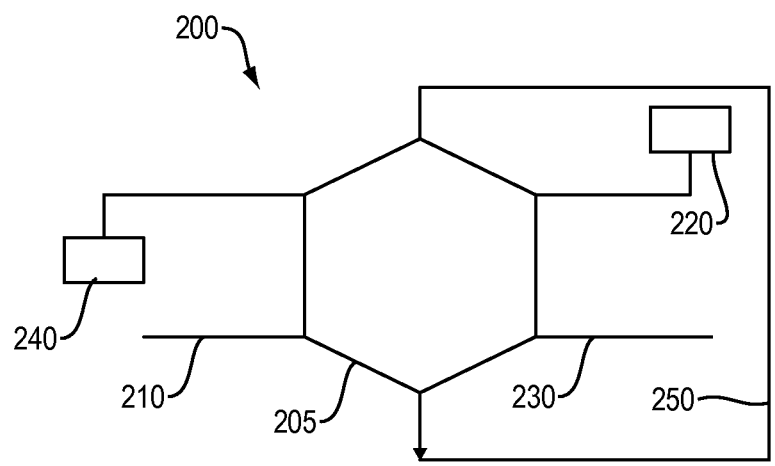
FIG. 2 is an illustration of an assembly for matching the flow rate between two devices.

In employing the devices discussed above to measuring electrical properties of particles isolated by microfluidic devices such as the device shown in FIGS. 1A-1D, there is typically a need for a flow rate matching device configured to match the flow rate of the microfluidic device with the flow rate of the electrical measurement device configured to measure an electrical property of the isolated particles, to make the relatively high flow rate of the microfluidic device (on the order of mL/min) compatible with the relatively low flow rate of the electrical property measurement device (on the order of μL/min, such as in the range of between about 0.25 μL/min and about 2 μL/min). There is a variety of different possible flow rate matching devices configured to match the flow rate, which would generally involve diverting at least some of the flow from the upstream high flow rate device into a reservoir to hold the excess fluid. An example of a reservoir assembly is shown in FIG. 2. The reservoir assembly 200 has an input 210 for the isolated particles, a second input 220 for an additional input fluid, such as a buffer (e.g., phosphate buffered saline (PBS)), an output 230 for the isolated particles to connect to the downstream electrical property measurement device, and a diverting output to an excess flow container 240 to hold excess fluid. In this aspect, a six-way valve 205 (e.g., Upchurch Scientific 6-Port Medium Pressure Injection Valve, Model V-450, Oak Harbor, Wash.) selects between flow patterns among the several components shown in FIG. 2.

As discussed above, a variety of particles can be isolated and have their electrical properties measured. If the particles are cells, such as leukocytes, that are prone to sticking to surfaces, then there are several techniques to keep the leukocytes from sticking to the components of the reservoir assembly. For example, the particles can be made to continuously move or flow. For example, if the volume of the fluid containing the leukocytes is on the order of several milliliters, then stirring of the fluid is possible. If the fluid volume is on the order of microliters (e.g., a drop of blood), then an injection loop 250, as shown in FIG. 2, can be used to keep the isolated particles flowing in a continuous flow at a flow rate in a range of between about 1 ml/min and about 0.0005 ml/min, such as between about 1 ml/min and about 0.005 ml/min, between about 1 ml/min and about 0.05 ml/min, between about 1 ml/min and about 0.5 ml/min, between about 0.1 ml/min and about 0.0005 ml/min, between about 0.01 ml/min and about 0.0005 ml/min, or between about 0.001 ml/min and about 0.0005 ml/min.

Figure 3:
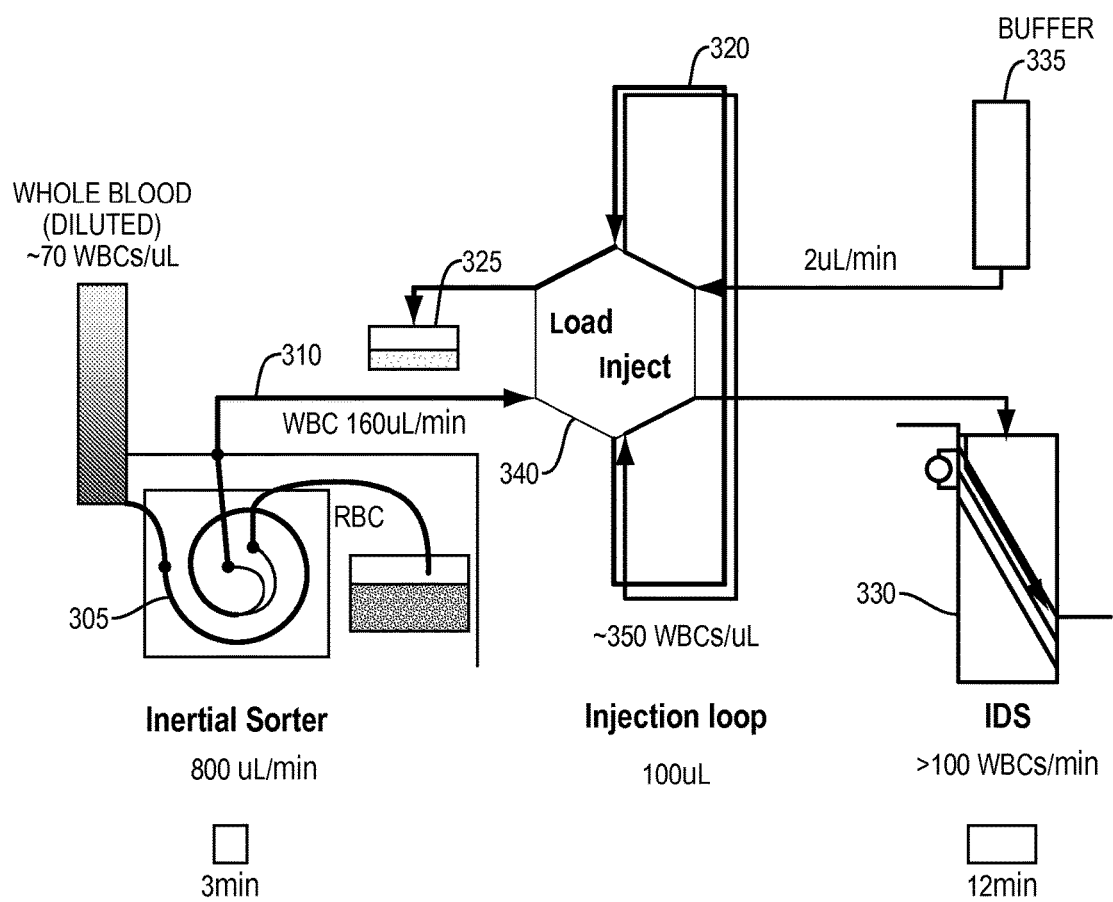
FIG. 3 is an illustration of an microfluidic device configured to isolate particles from a mixture connected to an iso-dielectric separation (IDS) device, with an assembly for matching the flowrate between the two devices in fluid communication with the two devices.

An example of an integrated system is shown in FIG. 3. The spiral inertial sorter 305 (such as the microfluidic device having a trapezoidal cross-section shown in FIGS. 1A-1D) dilutes whole blood and then isolates leukocytes from the sample, resulting in depletion of 99% erythrocytes and 5-fold enrichment of leukocytes. In the microfluidic device 305 shown in FIG. 3, the output resistance of the white blood cell outlet (WBC) was increased by having a longer shallow channel at the WBC outlet, as compared to prior microfluidic devices having a trapezoidal cross-section (see L. Wu et al., Analytical chemistry, vol. 84, no. 21, pp. 9324-31, November 2012, which is hereby incorporated by reference in its entirety), thereby increasing the concentration of WBCs, to a concentration of about 500,000 WBCs/mL. In this embodiment, the WBC outlet had a width of about 108 μm, a height of about 70 μm, and a length of about 15 mm. The RBC outlet had a width of about 300 μm, a height of about 100 μm, and a length of about 10 mm. In the microfluidic device 305, the flow rate ratio between the inner outlet (WBCs) and outer outlet (RBCs) is in a range of between 1:9 and 1:10. In a particular aspect, the flow rate of white blood cells was about 160 μL/min.

As shown in FIG. 3, in one embodiment, the isolated leukocytes 310 are stored in the injection loop 320 prior to introduction into or examination by the iso-dielectric separation device (IDS) 330. The amount of isolated leukocytes stored and flowing continuously around in the injection loop 320 is determined by the volume of the injection loop 320. Excess fluid from the microfluidic device 305 is stored in excess flow container 325. In one position of the six-way valve 340, buffer fluid 335 flows continously at a flow rate in a range of between about 0.25 μl/min and about 2 μl/min, such as between about 0.5 μl/min and about 2 μl/min, between about 1.0 μl/min and about 2 μl/min, or between about 1.5 μl/min and about 2 μl/min, for example, about 2 μL/min, into the IDS device 330. In another position of the six-way valve 340, the isolated leukocytes stored in injection loop 320 are pushed by buffer fluid 335 into the IDS device 330. In IDS, the cells flow in a shallow microfluidic channel with conductivity gradient and are deflected by a dielectrophoretic (DEP) force generated by slanted electrodes. The position where they pass through the electrodes is a measure of their electrical properties. See M. D. Vahey and J. Voldman, *High-throughput cell and particle characterization using isodielectric separation*, Analytical chemistry, vol. 81, no. 7, pp. 2446-55, (2009), which is hereby incorporated by reference in its entirety.

In the IDS, as shown in FIGS. 4a-d, a heterogeneous population of cells suspended in high conductivity media is loaded into a microfluidic chip. Other inlets containing intermediate and low conductivity media provide a parallel laminar co-flow. This configuration generates a conductivity gradient perpendicular to the main microfluidic channel flow. The channel also has slanted planar electrodes patterned at the bottom (single-sided IDS) or top and bottom (double-sided IDS). An AC electric field applied to the electrodes generates a DEP barrier that guides the cells across the conductivity gradient. Cells escape the DEP barrier at their isodielectric position (IDP), which is the position where they are at dielectric equilibrium with the surrounding medium. Cells with different effective permittivity (or effective conductivity) escape at a different IDP resulting in a transverse spatial distribution of cells. An optional CCD camera near the end of the channel takes videos of the cells. Finally, an optional image-processing software detects these cells and computes the resulting IDP distribution. The activation level of mouse leukocytes was measured using IDS and compared to traditional flow cytometry (FCM), showing a high correlation (see FIG. 5).

The integrated system with spiral sorter (i.e., microfluidic device 305) shown in FIG. 3 has advantages in efficiency over RBC lysing with traditional density gradient centrifuging methods, especially with respect to processing small volume samples of whole blood (on the order of microliters). The spiral sorter induces less activation than RBC lysis, providing a more accurate assessment of leukocyte activation by the downstream IDS. The injection loop 320 has low compliance and low resistance, allowing it to act as a reservoir to mitigate the flow rate mismatch between the spiral inertial sorter 305 and the IDS 330.

The system described above can be used for a variety of purposes. In one aspect, the system can be used to detect an inflammatory condition in an individual in need thereof. A method of detecting an inflammatory condition in an individual in need thereof includes introducing a sample from the individual comprising one or more white blood cells into a system, wherein the system comprises a microfluidic device that isolates the one or more white blood cells from the sample, an iso-dielectric separation (IDS) device that measures the iso-dielectric point of a cell (IDS device), and a reservoir configured to match flow rate from the microfluidic device to the flow rate of the IDS device, wherein the white blood cells are isolated from the sample in the microfluidic device, then introduced into the reservoir and maintained in the reservoir under conditions in which the flow rate of the one or more isolated white blood cells is matched to the flow rate of the IDS device, then introduced into the IDS device and maintained under conditions in which the iso-dielectric point (IDP) of the white blood cells is measured, and wherein a greater number of cells in the sample having a shift in IDP compared to a control indicates an inflammatory condition. The microfluidic device, reservoir, and IDS device are as described above. In one aspect, the shift in IDP is a shift to a higher IDP compared to the control. In another aspect, the shift in IDP is a shift to a lower IDP compared to the control. The shift to higher or lower IDP is also a function of the zero-reference for the IDP that the control is measured from.

In another aspect, the system can be used to detect leukocyte activation in an individual in need thereof. The method of detecting leukocyte activation includes introducing a sample comprising leukocytes into a system, wherein the system comprises a microfluidic device that isolates one or more leukocytes from the sample, an iso-dielectric separation (IDS) device that measures the iso-dielectric point of a leukocyte, and a reservoir configured to match flow rate from the microfluidic device to the flow rate of the IDS device, wherein the leukocytes are isolated from the sample in the microfluidic device, then introduced into the reservoir and maintained in the reservoir under conditions in which the flow rate of the one or more isolated leukocytes is matched to the flow rate of the IDS device, then introduced into the IDS device and maintained under conditions in which the iso-dielectric point (IDP) of the leukocytes is measured, wherein a shift in IDP of the leukocytes compared to a control indicates leukocyte activation. In one aspect, the shift in IDP is a shift to a higher IDP compared to the control. In another aspect, the shift in IDP is a shift to a lower IDP compared to the control. The shift to higher or lower IDP is also a function of the zero-reference for the IDP that the control is measured from. In one aspect, the control provides the IDP of unactivated leukocytes.

As will be appreciated by those of skill in the art, a variety of controls can be used. For example, the control can comprise white blood cells that are not activated and/or white blood cells obtained from one or more individuals that do not have an inflammatory condition (e.g., one or more healthy individuals). In one aspect, the control can be a reference standard, e.g., activated and unactivated white blood cells from e.g., healthy individuals not having an inflammatory condition, thereby providing the IDPs of activated and unactivated white blood cells. In a particular aspect, the method further includes monitoring of the inflammatory condition by measuring two or more samples over time. In a specific aspect, the individual is undergoing treatment for the inflammatory condition. A reduction in the number of white blood cells having a shift in IDP is an indication that the treatment is effective. A variety of inflammatory diseases can be monitored by the methods described herein. Examples include sepsis, Crohn's Disease, irritable bowel syndrome, and the like.

The methods described herein can be used to detect an inflammatory condition and/or leukocyte activation in minutes, e.g., about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 minutes.

EXEMPLIFICATION

Example 1

Overview of Systems and Methods

Sepsis is an uncontrolled activation of the immune system that causes an excessive inflammatory response. There is an unmet need to develop tools to monitor sepsis progression, which occurs quickly and provides few clues to indicate if treatment is effective. One molecular aspect of sepsis progression is leukocyte activation, which plays an important role in the immune response. Surface markers and cytokines are existing measures of leukocyte activation, however the time needed to assay them precludes their use in real time. An embodiment according to the present invention provides an integrated microfluidic system to measure the activation state of leukocytes from a drop of whole blood within 15 min, providing a simple assay to monitor sepsis progression with fine temporal resolution.

Figure 6A:
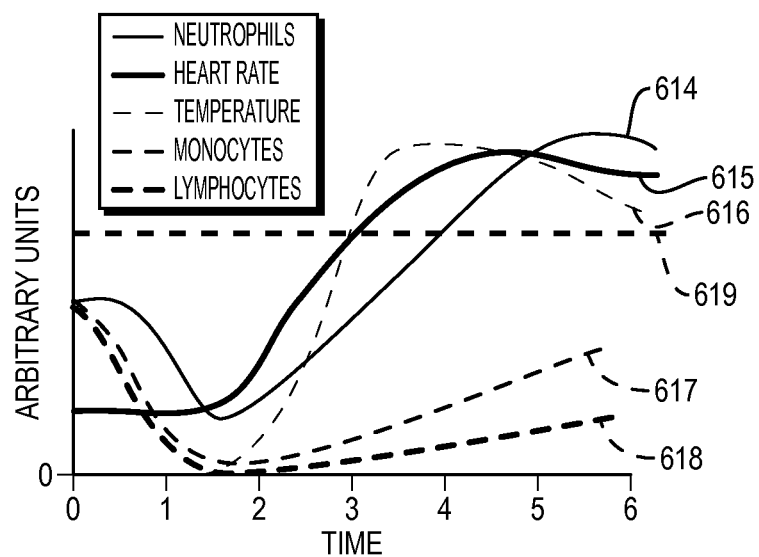
FIG. 6A is a graph illustrating sepsis dynamics by showing the development of five quantities over time.

FIG. 6A is a graph illustrating sepsis dynamics by showing the development of five quantities over time, in arbritrary units, namely neutrophils 614, heart rate 615, temperature 616, monocytes 617 and lymphocytes 618. See J. Cohen, "The immunopathogenesis of sepsis," *Nature*, vol. 420, no. 6917, pp. 885-91, 2002, the entire teachings of which are hereby incorporated herein by reference. The pathophysiology of sepsis involves multiple factors, both cellular and molecular, including bacteria, neutrophils, cytokines, etc.; and involves the activation of multiple cascases. Thresholds 619 can be defined for a diagnostic of sepsis, including, for example, a temperature between 36° C. and 38.3° C., a heart rate greater than 90 beats per minute, a respiratory rate greater than 20 breaths per minute, and a white blood cell count between $4 \times 10^9$ per liter and $12 \times 10^9$ per liter. For pathogen identification, timing is critical, and mortality increases after only a few hours. Current treatments include antibiotics and adjunctive treatments, such as those that improve supportive care, target the infecting factors and target the host response. In one solution that may be implemented in accordance with an embodiment of the invention, septic blood to be treated is removed from a patient to an extracorporeal device, where the blood undergoes filtration and quantification, after which the filtered blood is returned to the patient. In one embodiment according to the invention, a goal is to develop a system to measure leukocyte counts and leukocyte activation using electrical profiles of cells in higher temporal resoluation for monitoring sepsis progression.

Methods

Approach

Start with diluted whole blood (50 μL whole blood into 5 mL PBS)

Use inertial sorter to remove 90% RBCs and concentrate WBCs (~5 fold)

Capture isolated leukocytes in injection loop

Deliver leukocytes to isodielectric separation device (IDS) for counting and electrical measurement Features Require only 50 μL of sample Characterizing >1,000 leukocytes within 15 min Less activation than RBC lysing buffer Injection loop stores cells in flow condition and reduces risk of leukocytes sedimentation and sticking An example of the integrated system is shown in FIG. 3, above.

Characterization

Figure 6B:
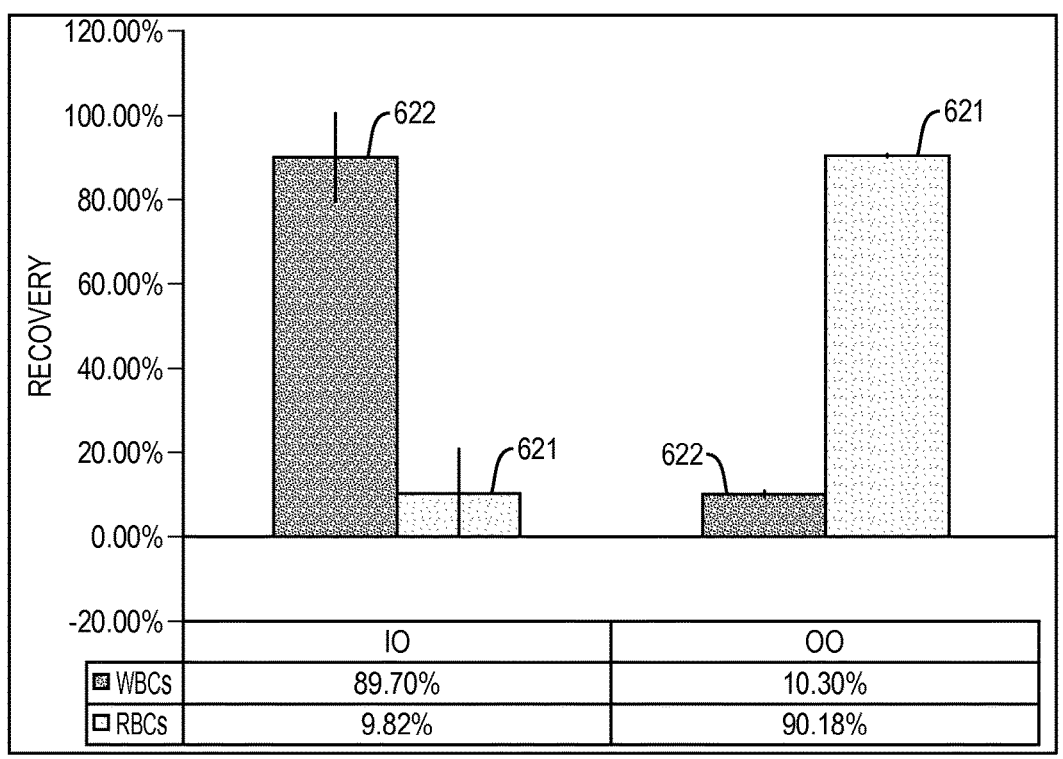
FIG. 6B is a graph of recovery percentage of red blood cells and white blood cells at each of an inside outlet (IO) and an outside outlet (OO) of a spiral sorter.
Figure 6C:
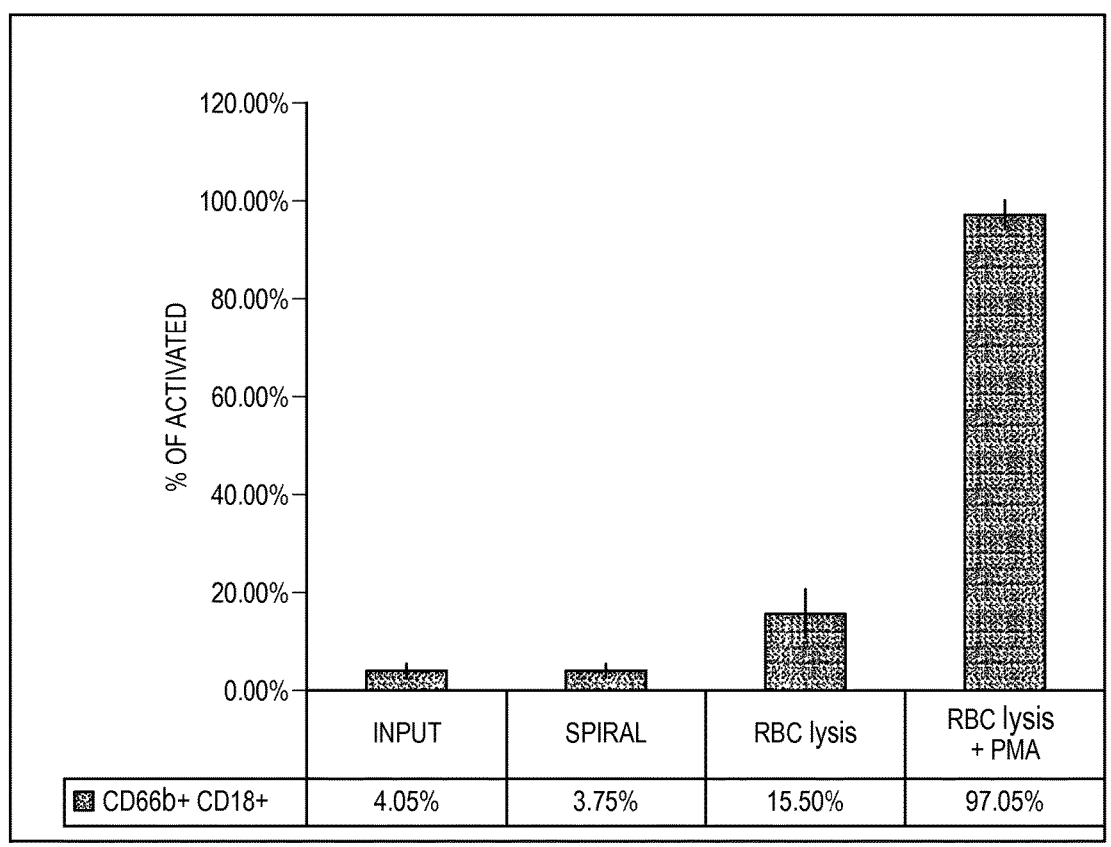
FIG. 6C is a graph of activation percentage of leukocytes for the input of a spiral sorter, the output of a spiral sorter, for RBC lysis, and for RBC lysis with PMA (Phorbol 12-Myristate 13-Acetate, Sigma Aldrich).

Performance characterization of a spiral intertial sorter, such as sorter 105 of FIG. 1, above, is shown in the graphs of FIGS. 6B and 6C. FIG. 6B is a graph of recovery percentage of red blood cells 621 and white blood cells 622 at each of an inside outlet (IO) and an outside outlet (OO) of the spiral sorter. It can be seen that about 90% of white blood cells 621 are recovered at the inside outlet, while about 90% of red blood cells 622 are recovered at the outside outlet. FIG. 6C is a graph of activation percentage of leukocytes for the input of the spiral sorter, the output of the spiral sorter, for RBC lysis, and for RBC lysis with PMA (Phorbol 12-Myristate 13-Acetate, Sigma Aldrich). It can be seen that the inertial sorter has little effect on leukocyte activation, while an RBC lysis buffer can activate leukocytes.

Figure 4:
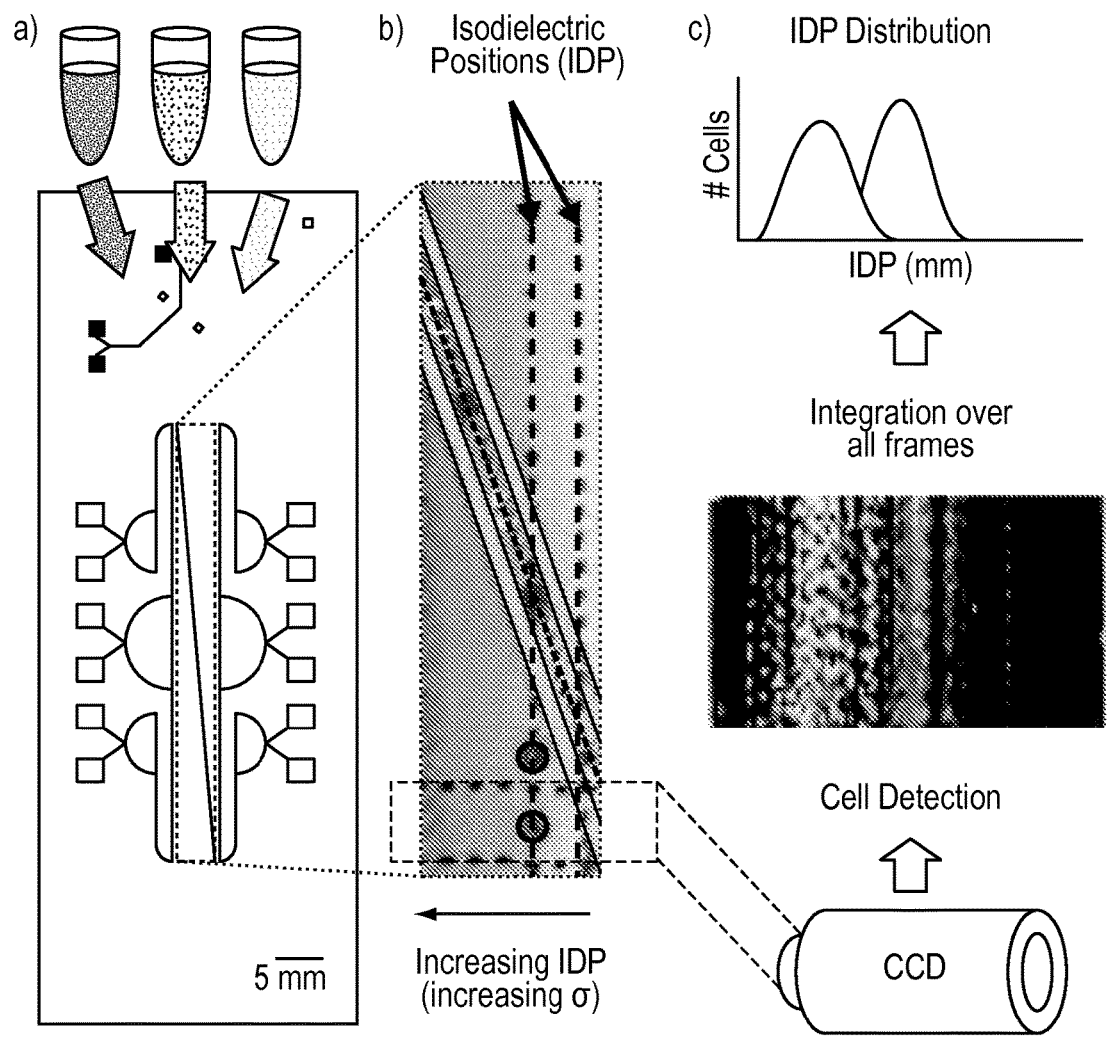
FIG. 4 a) is an illustration of a double-sided IDS device consisting of patterned electrodes on two glass substrates bonded together by a 25 µm thick double-sided tape.
Figure 6E:
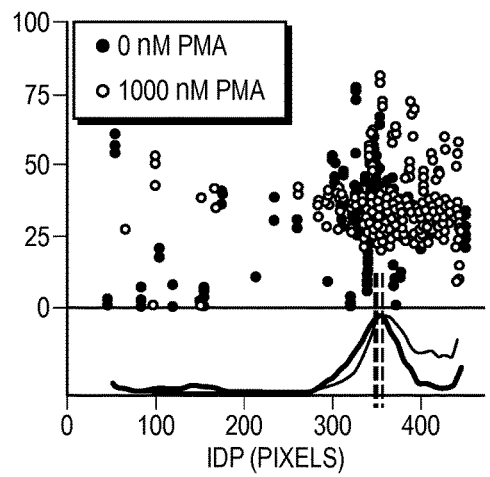
FIGS. 6D-6F are graphs showing that electrical profiling at high frequencies, such as greater than about 5 MHz, can be used for measuring leukocyte activation.
Figure 6D:
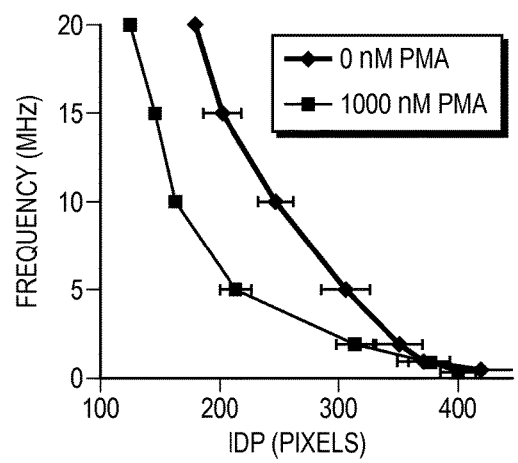
Figure 6F:
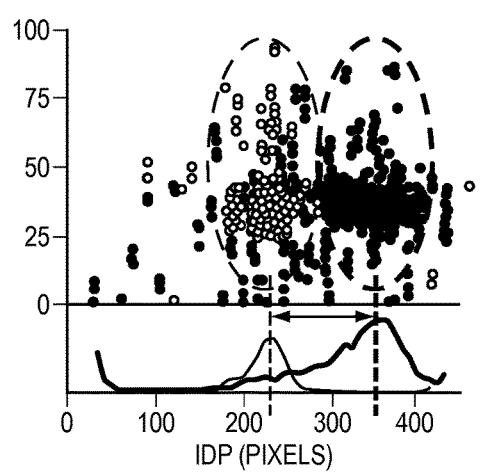

In addition, with reference to FIG. 4, above, leukocyte activation and counts can be measured using iso-dielectric separation (IDS). FIGS. 6D-6F are graphs showing that electrical profiling at high frequencies, such as greater than about 5 MHz, can be used for measuring leukocyte activation. In these graphs, two neutrophil populations were used: those treated with 1000 nM PMA (Phorbol 12-Myristate 13-Acetate, Sigma Aldrich), which were thereby activated; and those not treated with PMA, which were therefore non-activated. FIG. 6D shows a range of frequencies in MHz, from 0 to 20 MHz (on the vertical axis) versus iso-dielectric point (IDP) measurements (pixels); FIG. 6E shows arbitrary units (vertical axis) versus IDP (horizontal axis, in pixels) at 1 MHz; and FIG. 6F shows arbitrary units (vertical axis) versus IDP (horizontal axis, in pixies) at 5 MHz. It can be seen from these graphs of FIGS. 6D-6F that activated neutrophils can be filtered from flood at greater than about 5 MHz.

Figure 5:
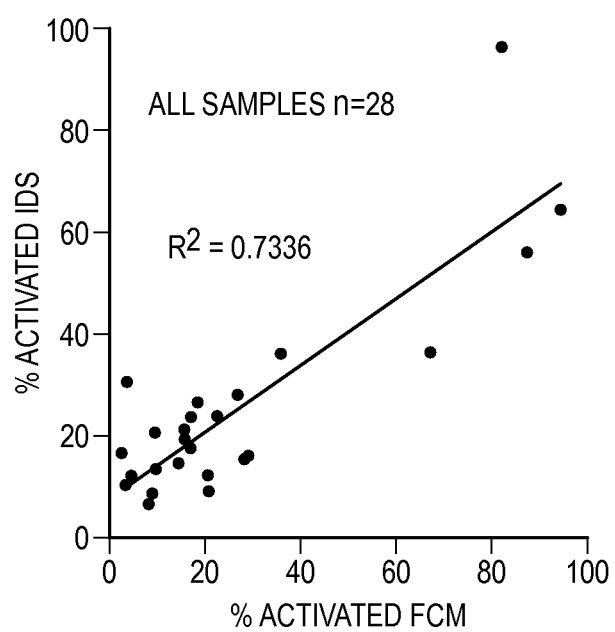
FIG. 5 is a graph of % activation obtained by IDS and by flow cytometry (FCM).

In addition, as discussed relative to FIG. 5, above, IDS counts are linearly correlated with flow cytometry, and thus promising for use to estimate white blood cell concentration.

In accordance with an embodiment of the invention, the integrated system of FIG. 3 has been used to show that RBC's can be removed, and WBC concentrated, to levels suitable for IDS.

Figure 6G:
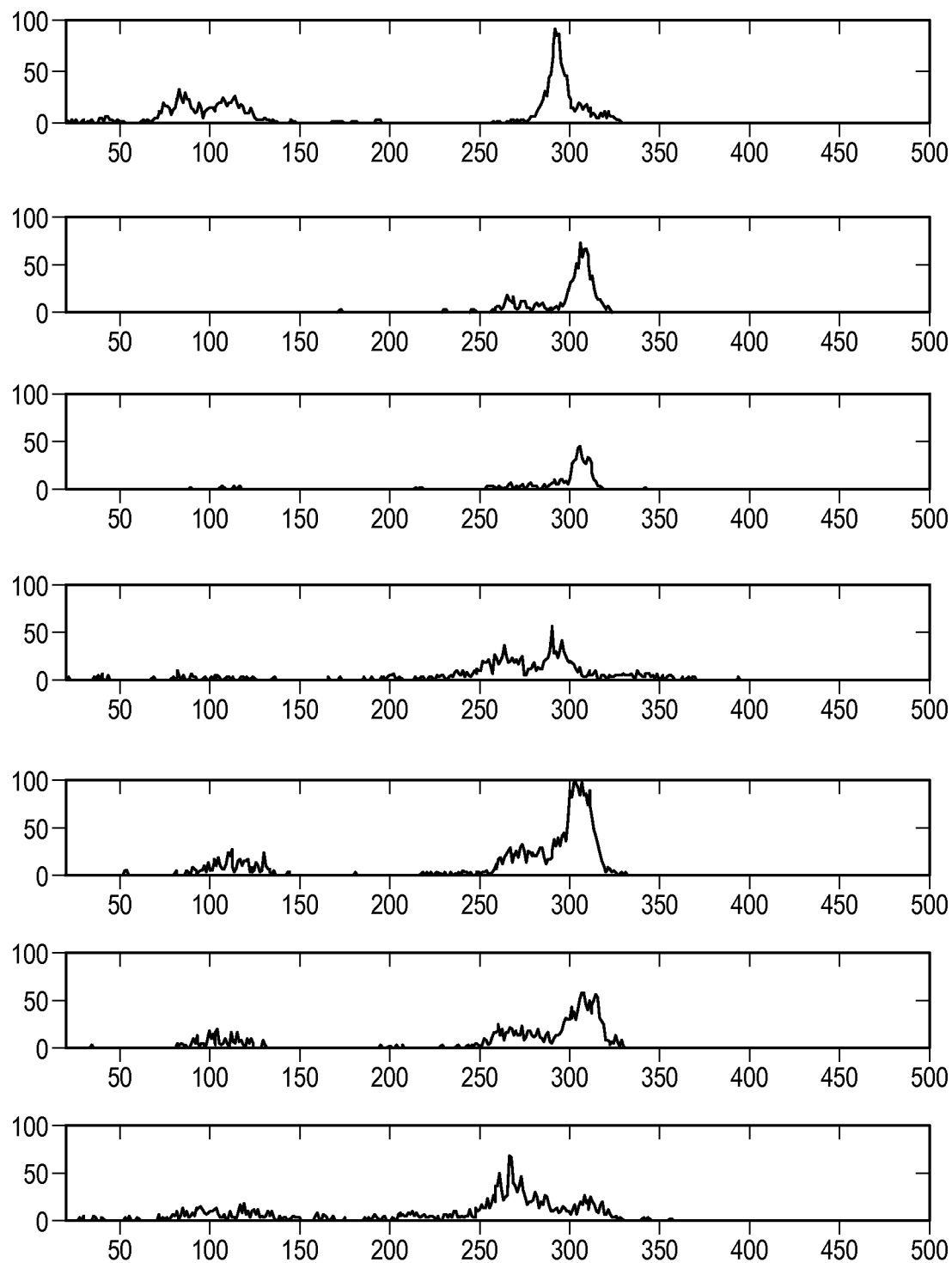
FIG. 6G shows seven successive graphs, over time, of iso-dielectric point (IDP) in arbitrary units at 10 MHz, thereby illustrating activation of leukocytes from whole blood with 30 minute time resolution.

In addition, activation of leukocytes from whole blood has been measured with 30 minute time resolution. FIG. 6G shows seven successive graphs (from top to bottom), over time, of iso-dielectric point (IDP) in arbitrary units at 10 MHz. Leukocyte subpopulation shift left (indicating activation) can be seen starting at the 2-hour time point (fourth measurement down from top).

Summary

In accordance with an embodiment of the invention, an integrated system has been developed that can measure the electrical properties of >1000 leukocytes within 15 min from a drop of whole blood to result, enabling monitoring electrical property changes of leukocyte activation with high temporal resolution.

Measurements were made from 50 µL of human whole blood each time for 7 times consecutively without fouling. This system has potential as a point-of-care device for monitoring sepsis and other inflammatory diseases.

Example 2

Monitoring Sepsis Using Electrical Cell Profiling

Sepsis is a potentially lethal condition that would benefit from early monitoring of activated leukocytes for faster treatment and improved prognosis. As shown herein, characterization of the intrinsic electrical properties of leukocytes provides a quick way to quantify the number of activated cells as sepsis progresses. Iso-dielectric separation (IDS) uses dielectrophoresis (DEP) to characterize the electrical signatures of cells. Here IDS is used to show that activated and non-activated cells have different electrical properties and that a double-sided version of the IDS platform is then presented to rapidly characterize thousands of cells. This platform is less prone to cell fouling and allows faster characterization. Using samples from a cecal-ligation and puncture (CLP) model of polymicrobial sepsis in mice, the number of activated leukocytes was estimated by looking into differences in the electrical properties of cells. It is shown herein using animal models that electrical cell profiling correlates with flow cytometry (FC) results and that IDS is therefore a good candidate to provide rapid monitoring of sepsis by quantifying the number of activated leukocytes.

Sepsis is a potentially lethal condition (~30% mortality) that represents a systemic inflammatory response to infection. In many cases, circulating bacteria can be detected in the blood, which induces complex immune responses that are initially pro-inflammatory and later anti-inflammatory. At the center of these evolving inflammatory responses are leukocytes. Granulocyte recruitment and activation, for instance, increase with the initial inflammatory response associated with sepsis.

Granulocyte mobilization can occur within a matter of hours, therefore rapid quantification of activated leukocytes, and activated circulating granulocytes in particular, can provide a real-time indicator of host responses to sepsis progression and would allow faster treatment and improve prognosis.

Blood cells are routinely counted and characterized in clinical settings as a diagnostic aid to identify septic patients. This requires counting subsets of cells from a complex heterogeneous population such as septic blood. Clinicians often use complete blood counts (CBC) that have little specificity. Identifying sepsis, however, requires a more specific count able to identify banded forms and activated leukocytes. This is done via extrinsic labeling that uses probes added to the cells to molecularly distinguish the subpopulations. This antibody-based labeling, however, requires close to one hour of sample preparation, which prevents fast quantitation of activated leukocytes and impedes detailed monitoring of the early stages of sepsis.

Intrinsic properties, meanwhile, refer to physical properties including size, mechanical properties, etc. These properties do not need exogenous labels and do not require long preparation steps to become apparent.

Here, firstly, the electrical properties of activated human granulocytes were characterized at a single cell level using a traditional single-sided IDS platform. This characterization successfully classified activated and non-activated granulocytes. Secondly, technical innovations were presented on a double-sided IDS platform that allowed increased flow rates and a more robust usage with samples prone to fouling. This IDS platform was then used to characterize samples from septic mouse models and determine a classification threshold for activated and non-activated granulocytes. Finally, it was shown that electrical profiling of primary cells from a septic mouse model correlates with FC analysis and could therefore be used to monitor sepsis progression.

Materials and Methods
Experimental Setup

In IDS, a heterogeneous population of cells suspended in high conductivity media was loaded into a microfluidic chip. Other inlets containing intermediate and low conductivity media provided a parallel laminar co-flow. This configuration generated a conductivity gradient perpendicular to the main microfluidic channel flow. The channel also had slanted planar electrodes patterned at the bottom (single-sided IDS) or top and bottom (double-sided IDS). An AC electric field applied to the electrodes generated a DEP barrier that guided the cells across the conductivity gradient. Cells escaped the DEP barrier at their isodielectric position (IDP), which is the position where they are at dielectric equilibrium with the surrounding medium. Cells with different effective permittivity (or effective conductivity) escaped at a different IDP resulting in a transverse spatial distribution of cells. A CCD camera near the end of the channel took videos of the cells. Finally, image-processing software detected these cells and computed the resulting IDP distribution (see FIGS. 4a-4d).

IDS Operation

To determine the IDP different populations, suspensions ($2 \times 10^6$ cells/ml) in PBS buffer with a conductivity of 1.2 S/m (PBS, 1% BSA, 1 u Heparin) were used. For the intermediate and low conductivity media, this buffer was mixed with an isotonic sucrose solution to achieve an intermediate conductivity of 0.8 S/m and a low conductivity of 0.4 S/m.

External syringe pumps controlled the flow in all three inlets (see results below for detailed flow rate conditions). The cell inlet connected to a custom made fluidic switch (including a valve, such as a 6-Port Medium Pressure Injection Valve, Upchurch Scientific Model V-450, Oak Harbor, Wash.) allowed device priming and cleaning between samples and helped avoid fouling.

A function generator (Agilent 33220A) and an amplifier applied a 10 Vpp AC field with the same amplitude across all frequencies. A CCD camera at the end of the main channel imaged fluorescently labeled cells flowing across the field of view. An image detection script analyzed the videos to detect cells in each frame and determine the centroid of each cell. The same script generated cell position distributions that correspond to the resulting IDP distribution.

Device Fabrication

The fabrication of the single-sided IDS platform has been described previously. See M. D. Vahey and J. Voldman, Anal. Chem., 2008, 80, 3135-3143. Briefly, soft lithography techniques and replica molding were used to generate a 2 mm wide and 20 µm tall microchannel that was bonded to a glass substrate with patterned electrodes. One used e-beam evaporation of 100 Å of Ti and 2000 Å of Au and a lift-off process, which generates interdigitated metal electrodes with gap and width of 15 µm and 50 µm, respectively.

The double-sided IDS consists of a microchannel cut in a double sided tape sandwiched by two of these glass slides with patterned electrodes. The fabrication is similar to previously reported devices. See M. Evander, A. J. Ricco, J. Morser, and G. Kovacs, Lab on a Chip, 2012. A 2 mm wide microchannel was cut using a laser cutter on a 25 µm double-sided tape (PSA tape, Adhesive Research). The tape was aligned to the substrate under a stereoscope and pressed with a rubber roller to bond the channel to one of the substrates (bottom glass slide). 2 mm holes were drilled using diamond bits on the other substrate (top glass slide) to allow fluidic access to the microchannel. The top substrate was then aligned and pressed onto the topside of the tape. The whole device was then set in a hotplate (90° C.) for 1 h with 1 kg weight on top to ensure a proper seal.

In both platforms, electrode connections consist of wires attached to electrode pads using silver epoxy.

CLP Septic Mouse Model

A murine cecal ligation and puncture (CLP) was used as a polymicrobial sepsis model. Mice with a femoral arterial catheter line were used.

Briefly, for the CLP intervention a one-cm incision was made in the mid-lower abdomen and the cecum was exposed, ligated to preserve intestinal continuity, and two punctures are made distal to the ligation. The ligated cecum was placed back in the peritoneal cavity and the subcutaneous tissue was closed. Small aliquots of 100 microliters of blood were collected at 6, 12 and 24 h.

Cell Preparation 10 ml samples of heparinized human blood were obtained from healthy donors (Blood Research Components, LLC). Two aliquots of 5 ml of blood were set in 3 ml of Mono-Poly Resolving Medium (MP Biosciences) and the samples were spun in a free hanging centrifuge at 400 cfg for 40 min. The resulting layered samples contained a band of granulocytes that were recovered and triple washed with a PBS solution. Finally, the cells were resuspended in a PBS solution (PBS, 1% BSA, 1 u Heparin).

Human granulocytes were activated with different concentrations of PMA (Phorbol 12-Myristate 13-Acetate, Sigma Aldrich) in a PBS solution with $Mg^{++}$ and $Ca^{++}$. To activate the cells, a 1:1 solution of suspended cells was mixed with PMA buffer and the resulting suspension was incubated for 20 min at room temperature.

Mouse leukocytes were obtained from blood aliquots collected from the mouse models. Whole blood was mixed with lysis buffer for 5 min and then triple washed in a PBS solution and resuspended in the same PBS solution described above.

A 50 µM solution of nuclear dye (SYTO-9, Invitrogen) was used with all types of cells to aid visualization of nucleated cells and simplify cell detection in the image processing steps. In all cases, $2 \times 10^6$ cells/ml solutions of stained cells were loaded into the IDS device immediately after preparation.

Flow Cytometry and Functional Assays of Leukocytes

Flow cytometry (FC) was performed with a BD Accuri (Becton Dickinson) flow cytometer with a 488 nm and a 670 nm emitter. Granulocytes were gated based on side and forward scatter and stained with anti-human CD11b-PE, anti-human CD66b-PerCP-CY5.5 and anti-human CD18-FITC (Becton Dickinson) as activation indicators. Mouse samples were stained using anti-mouse CD-18 and anti-mouse Ly6G as an activation marker.

Results

Dielectric Characterization of Human Granulocytes

The first goal was to confirm that IDS is able to discern IDP differences in activated and non-activated human granulocytes extracted from freshly collected blood. As a way to control the activation level, one used PMA, which is commonly used to activate granulocytes in vitro. Different doses of PMA resulted in increased CD11b and CD18 expression as well as increased levels of reactive oxygen species, which indicate granulocyte activation.

Figure 7:
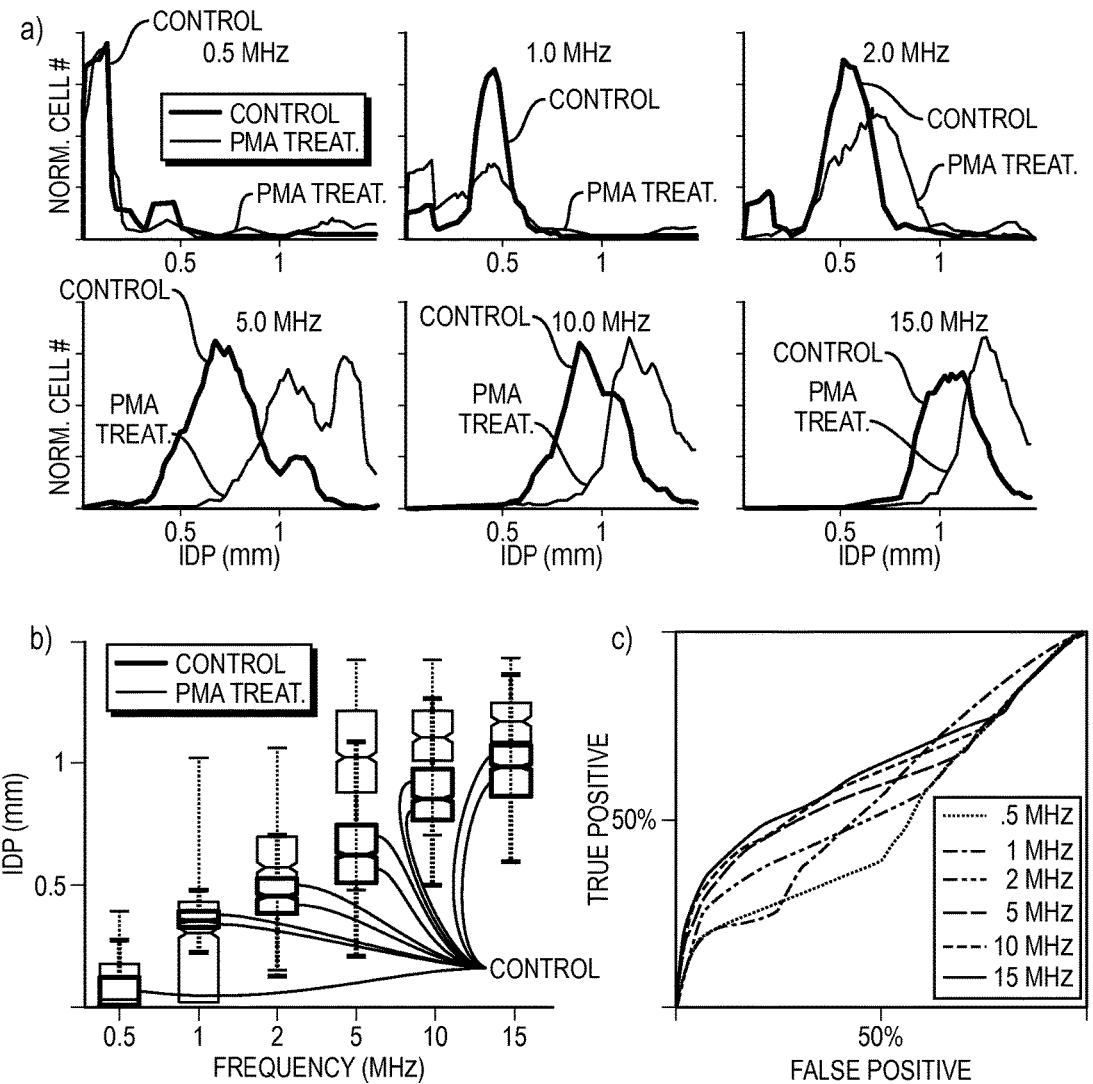
FIG. 7a) shows representative IDP distributions of PMA treated and control populations of granulocytes. The distributions are displaced to higher IDP as the applied frequency increases
FIG. 7(b) shows that IDP distributions of activated and non-activated granulocytes differ at frequencies >5 MHz (** D-Statistic>0.6).
FIG. 7(c): ROC curves using IDP as a classification criteria show an area under the curve >0.6 above 5 MHz.

Using a single-sided IDS platform, the IDP distributions of granulocytes treated with 1 µM PMA and a control population of non-treated granulocytes were examined. A 10 Vpp AC voltage was applied to the electrodes with frequencies ranging from 0.5 MHz to 15 MHz. Cells were loaded at 0.4 µl/min and the intermediate and low conductivity buffer at 0.55 µl/min (1.5 µl/min total). To determine the IDP distributions for each frequency, the IDP distributions of at least 1000 cells were recorded, which required an acquisition of about 1.5 min. FIG. 7 shows the results of three independent samples evaluated throughout three different days.

At low frequencies both PMA treated and non-PMA treated populations have similar IDP distributions. As frequency increases, however, the IDP distribution of activated granulocytes is displaced towards higher IDP (FIG. 7a). This can be shown by performing a Kolmogorov Smirnov test for each pair of distributions at each frequency. A D-statistic greater than 0.6 for frequencies can be seen above 5 MHz (FIG. 7b).

Given that the IDP distributions of PMA treated and non-treated populations are different it was decided to use the IDP position of cells as a threshold to classify cells into activated and non-activated. Receiver-operator characteristics (ROC) are a standard method for assessing if a given test is able to discern two different populations. The IDP was used as a classification threshold and the original population was used to determine true positives (i.e., PMA treated cells=activated cells). The resulting ROC curves have an area-under-the-curve (AUC) that increases with higher frequencies (see FIG. 7c). The peak AUC occurs at frequencies ranging from 10-15 MHz with a value of 0.62, suggesting that at high frequencies IDP is able to distinguish PMA-treated vs. non-treated human granulocytes.

Double-Sided IDS

IDS is a good candidate to monitor sepsis since it can analyze cells continuously. To monitor sepsis progression, however, multiple samples needed to be analyzed within minutes. Single-sided IDS is used at low flow rates and it generates a net upward force pushing cells to the top of the channel where they often contact the channel ceiling. These conditions make the use of single-sided IDS challenging over prolonged periods of time when combined with the inherent fouling and clotting properties of activated granulocytes. In fact, multiple samples had to be discarded while characterizing human granulocytes due to cells sticking to the microchannel walls and electrodes.

Moreover, one wanted to characterize septic mouse blood, which has cells with a smaller diameter. The magnitude of DEP forces decreases with cell size as $R^3$. Therefore, deflecting mouse cells with IDS would require a lower flowrate, which would make evaluating mouse samples more challenging.

A double-sided IDS was fabricated, based on previous work that had used microfluidic chips with electrodes on the top and bottom of the channel. This configuration has the advantage of centering cells vertically, which in this case helps reduce cell adhesion to the microchannel walls.

Figure 12:
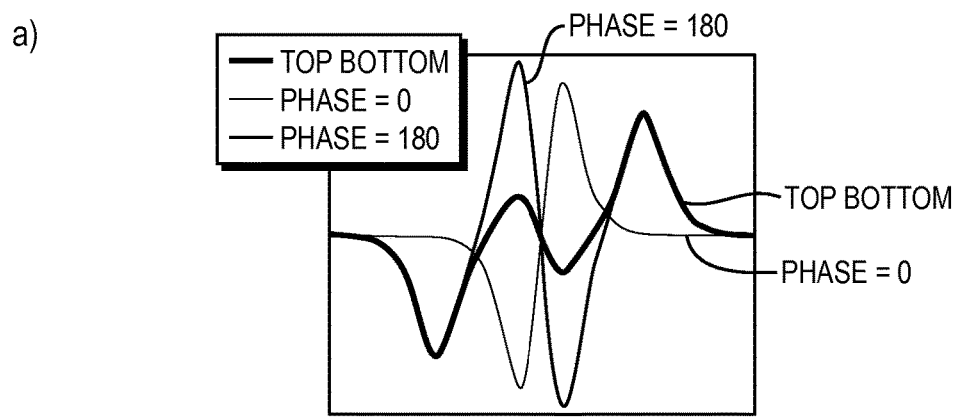
FIG. 12(a) shows that the magnitude of the DEP force is higher in a top bottom configuration.
FIG. 12(b) thEHD and iEHD effects do not dominate at the voltages used.
FIG. 12(c) shows that the resulting DEP force centers cells in the middle of the channel.
Figure 12:
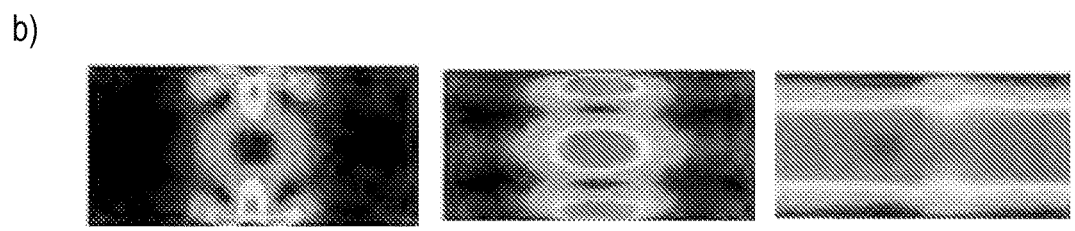
Figure 12:
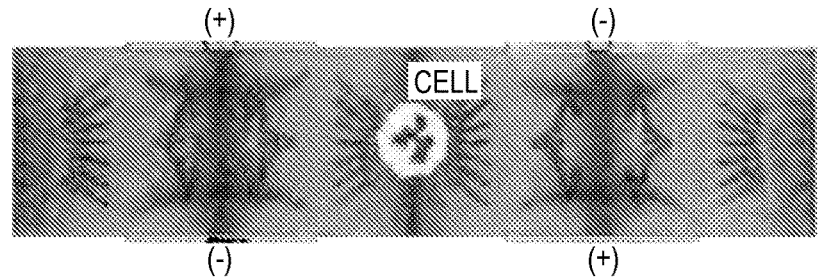

Considering the particular geometry, cell size and applied voltage, the system was simulated and it was estimated that a double-sided configuration would double the maximum flow rate that could be used. An FEM simulation also shows that this configuration in the nDEP regime pushes cells to the minimum electric field in the middle of the channel (see FIG. 12). Both the increased flow-rate and minimizing cell-wall contact decrease cell adhesion to the chip.

Qualitatively less fouling was seen while using the double-sided IDS, which allowed faster operation and longer sampling periods. To quantify this improvement it was decided to use leukocytes from mice and assess the stability of the IDP distribution over the entire sampling period. The cells as well as the intermediate and low conductivity buffer were loaded at 1 μl/min to achieve a total flowrate of 3 μl/min. This flowrate enabled an increase in the sampling periods to 5 min intervals without fouling and therefore quadrupled the number of cells characterized per sample (at least 4000 cells).

Figure 8:
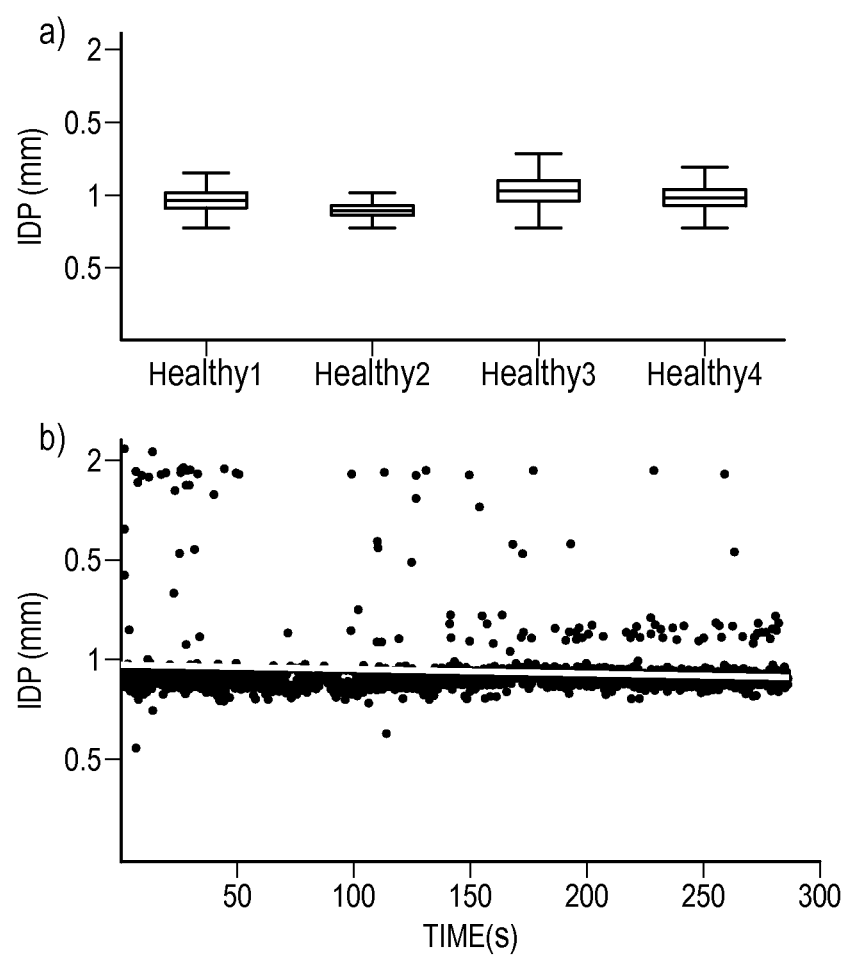
FIG. 8(a) shows that IDP distributions at 10 MHz are similar across multiple animals and weeks.
FIG. 8(b) shows representative time series of the IDP for a healthy animal. The distribution is stable across the entire sampling period of 5 min. A linear regression (red line) has an approximately flat slope (−2.3e-4 mm/s).

The characterization of 4 healthy mice at 10 MHz resulted in tight distributions with a mean IDP of 1.04±0.05 mm (see FIG. 8a). This shows that characterization with the double-sided IDS is consistent across multiple samples and weeks. FIG. 8b shows a representative experiment. The IDP distribution does not vary over time and a linear regression has virtually no slope (−2.3e-4 mm/s). Outlier cells are indicative of the intrinsic heterogeneity in primary samples from healthy animals.

Monitoring Septic Blood

A controlled pre-clinical model of sepsis was then used as a way to compare traditional phenotyping with characterization using the double-sided IDS platform. Specifically, blood samples were obtained from a cecal-ligation and puncture (CLP) model of polymicrobial sepsis in mice.

Blood samples were obtained from healthy mice and from septic mice at 6 h, 12 h and 24 h after the cecal ligation, and the number of Ly6G+ and CD-18+ granulocytes was measured using flow cytometry (FC). Samples from the same animals were also characterized using the double-sided IDS platform and both results were compared (see FIG. 9a).

Figure 9:
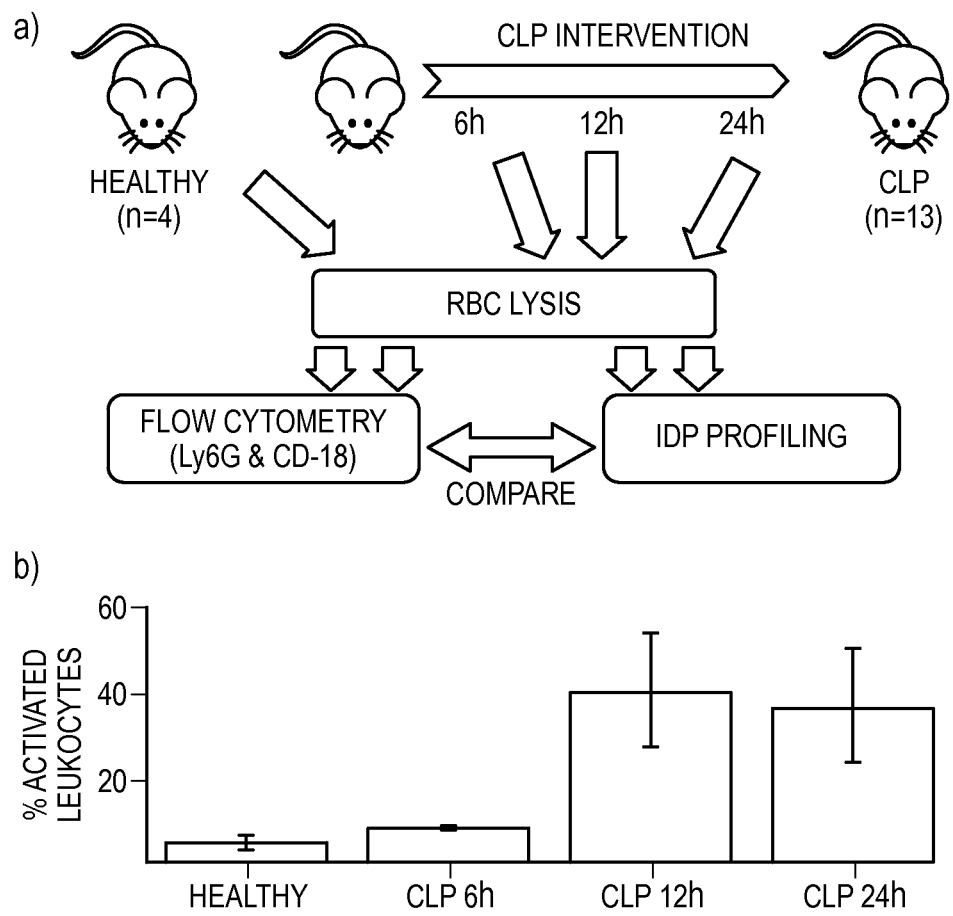
FIG. 9(a) shows experiments consisting of comparing flow cytometry (FC) results and IDP distributions of blood samples. Samples come from healthy mice and septic mice at different time points after the CLP intervention.
FIG. 9(b) shows results from FC indicating that the percentage of activated leukocytes increases with time.

FC results showed that the number of activated granulocytes increases over time (as shown in FIG. 9b). There is, however, great variability between samples in septic mice. This variability is a result of the complexity of the septic response and the different prognosis of each animal.

Figure 10:
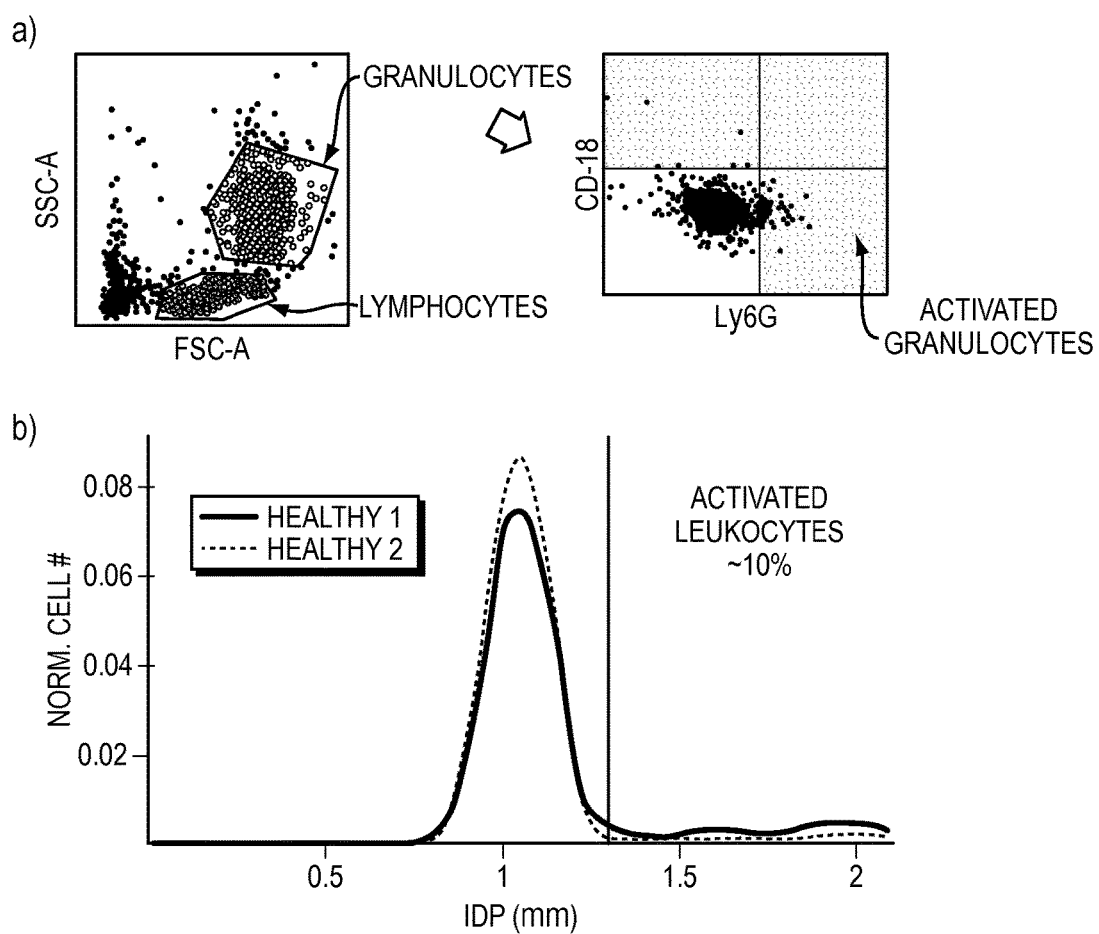
FIG. 10(a) shows CD-18+ and Ly6G+ gates in FC set using healthy mice samples so that <5% of the cells are activated.
FIG. 10(b) shows a similar strategy followed to determine the gates for activated leukocytes in IDS where <10% of the cells of healthy animals are activated.

In order to compare the results provided by IDS and FC, classification gates were defined for both cases. In FC the number of activated cells is evaluated by setting a gate for CD-18+ and Ly6G+ cells (see FIG. 10a). This gate was chosen using two healthy animals and setting the gate so that no more than 10% of the cells fall within the activated group.

Based on the results obtained from activated human granulocytes, one would also expect to see a higher IDP for activated leukocytes in mice. As mentioned before, samples from healthy animals have a main peak in their IDP distribution at 1.04±0.05 mm with a few cells in secondary peaks with higher IDP. This information can be used to select a gating strategy in the IDP domain that would allow activated cell classification and quantification of the percentage of activated cells. Much like in FC, the assumption was made that the main peak represented un-activated cells and all cells with higher IDP were activated cells. As in FC, a gate was set to delineate the two populations by analyzing two healthy animals and having at least 90% of their cells fall within the non-activated group (see FIG. 10b). Importantly, after selecting these gates, they were then used for all animals across all experiments.

Using this gating strategy, the number of putative activated leukocytes in CLP mice samples was counted. The values varied, even for the same nominal injury, due to the inherent variability of the animal studies. Examining the IDP distributions for CLP animals one sees that they generally also have a main peak around 1 mm. In this case, however, the percentage of cells in the activated region is generally larger (see FIG. 11a). This is consistent with the hypothesis that cells with higher IDP represent activated cells, and that this percentage should increase as sepsis progresses.

Figure 11:
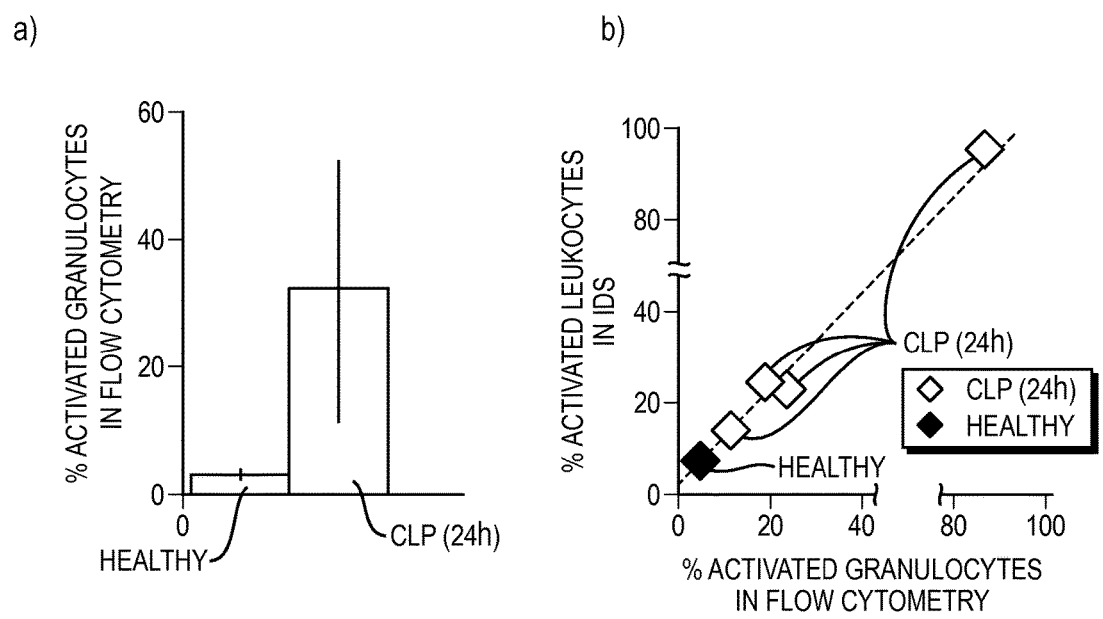
FIG. 11 shows graphs of FIG. 11(a): % activated granulocytes in flow cytometry.

Results were aggregated across 3 different weeks for a total of 18 animals (4 healthy, 4 CLP 6 h, 3 CLP 12 h and 7 CLP 24 h), and upon comparing the putative activated cells from IDS as compared to activation as measured with FC, a linear correlation was obtained with $R^2=0.79$ (see FIG. 11b). The correlation has a non-zero offset, possibly due to differences in selecting the initial gating for both methods. The slope was 0.68, likely because changes in IDP are due to biophysical changes that might change at a different rate than CD-18 and Ly6G expression.

Discussion

Differences in the electrical properties of cells are due to different biophysical mechanisms. Discerning these biophysical mechanisms is not the aim of this application, however, previous works and models have suggested that as frequency increases differences in inner cellular compartments become more apparent. In particular membrane differences are apparent at lower frequencies, while cytoplasmic and nuclear differences are apparent at higher frequencies.

The results above show that differences in activated and non-activated leukocytes are at mid-frequencies (5-15 MHz). This is most likely due to differences in the electrical properties that are associated with biophysical changes in the membrane or cytoplasm of the cell and that are related to cell activation.

Electrical cell profiling using IDS can be used exploit these differences and estimate the number of activated leukocytes in a given population. In turn, monitoring the number of activated circulating leukocytes can provide a marker that could be used to detect and/or monitor the progression of an inflammatory condition (e.g., sepsis). Overall, the results above show that the double-sided IDS platform is suitable for measuring IDP for such purpose and such use has been shown in mice at 6 h, 12 h and 24 h after a CLP intervention.

Clinical deployment of IDS, however, would require sampling at much closer time points. Even though one did not sample at finer time granularity due to logistical constraints, the current implementation of the double-sided IDS allows analyzing a sample within 30 min of collection. Most of this time is required for the necessary step of separating leukocytes from red blood cells (RBC) prior to loading into IDS. The actual analysis of the cells only requires about 10 minutes (e.g., 5 minutes of video acquisition and 5 minutes of nuclear cell stain and video processing).

Conclusions

It has been demonstrated that IDP identifies activated and non-activated human granulocytes and can be used to quantify each population at a single cell level. This could be used to monitor the evolution of septic blood by quantifying the percentage of activated leukocytes.

To deal with complex samples from septic blood, a double-sided version of the IDS platform has been implemented that allows increased flow rate operation and avoids cell fouling by vertically focusing cells at the middle of the channel. This new platform enabled quadrupling the number of cells characterized per sample.

Finally, it has been shown that IDS can be used to monitor septic blood from CLP mice. It was demonstrated that setting gates for cells with high IDP as a way to quantify activated leukocytes correlates with FC assays. Importantly, this correlation held across mice, across interventions, and across weeks. Thus, these results suggest that IDP profiling can quickly quantify activated leukocytes in clinically relevant animal models, and represent the first example of the use of electrical cell profiling that provides a clinically relevant metric.

Example 3

Dielectrophorectic Characterization of Activated Neutrophils for the Treatment of Sepsis As discussed above in Example 1, in accordance with an embodiment of the invention, septic blood to be treated is removed from a patient to an extracorporeal device, where the blood undergoes filtration and quantification, after which the filtered blood is returned to the patient. Further, in an embodiment according to the invention, a goal is to develop a system to measure leukocyte counts and leukocyte activation using electrical profiles of cells in higher temporal resoluation for monitoring sepsis progression.

Figure 13:
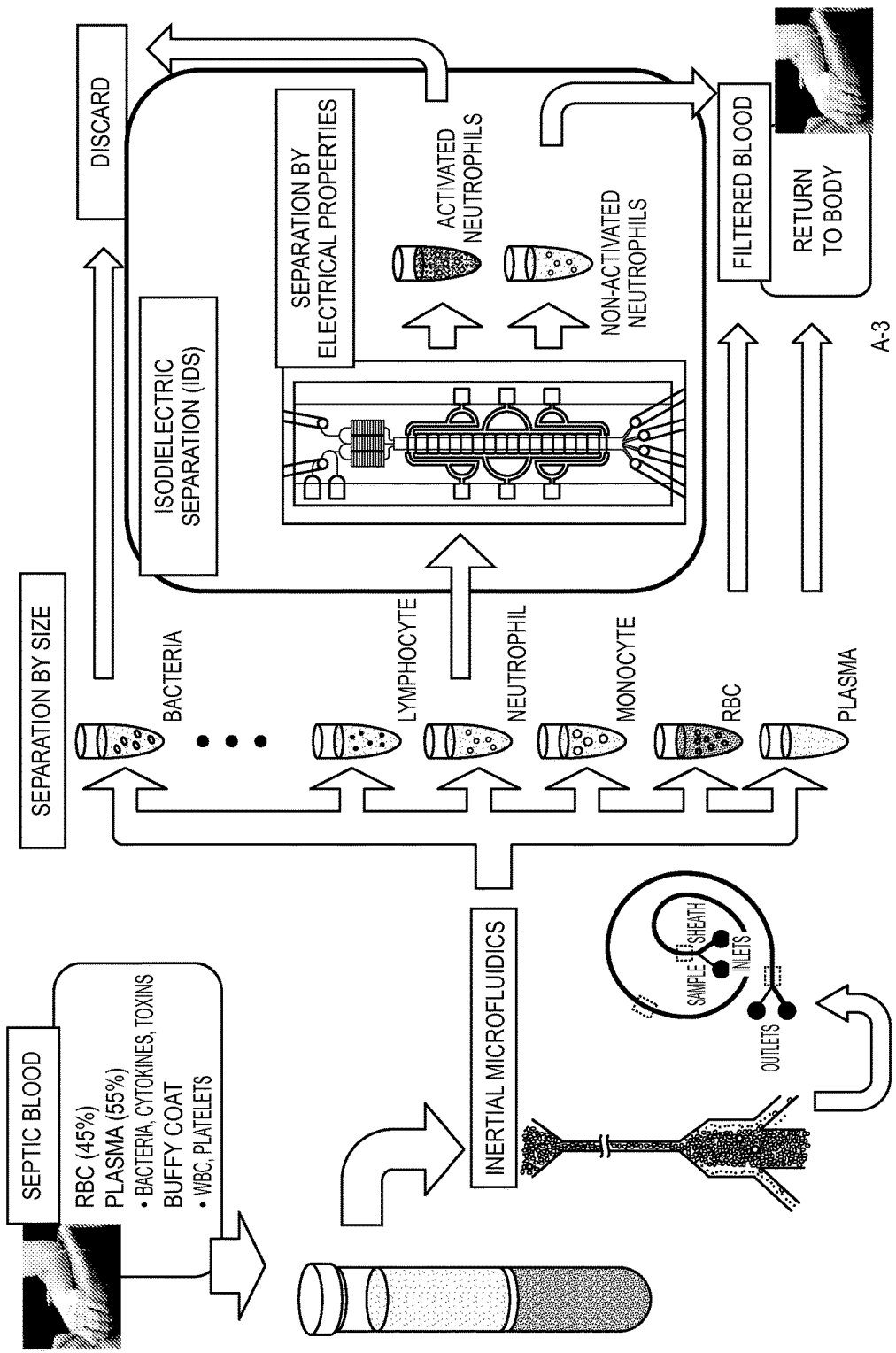
FIG. 13 is a schematic flow diagram of dialysis-like treatment and diagnosis of sepsis.

FIG. 13 is a schematic flow diagram of dialysis-like treatment and diagnosis of sepsis. Septic blood, which consists of about 45% RBC's, 55% Plasma (bacteria, cytokines and toxins) and a buffy coat (which includes WBC's and platelets) is removed from a patient and separated by inertial microfluidics. Blood components, including bacteria, lymphocytes, neutrophils, monocytes, RBC's and plasma are separated by size using the inertial microfluidics. Some components, such as bacteria, are discarded. Other components, such RBC's and plasma, are returned to the body. Other components, in particular the neutrophils, can be separated by electrical properties, for example by isodielectric separation (IDS). This results in activated neutrophils, which may be discarded, and non-activated neutrophils, which may be returned to the body.

Figure 14A:
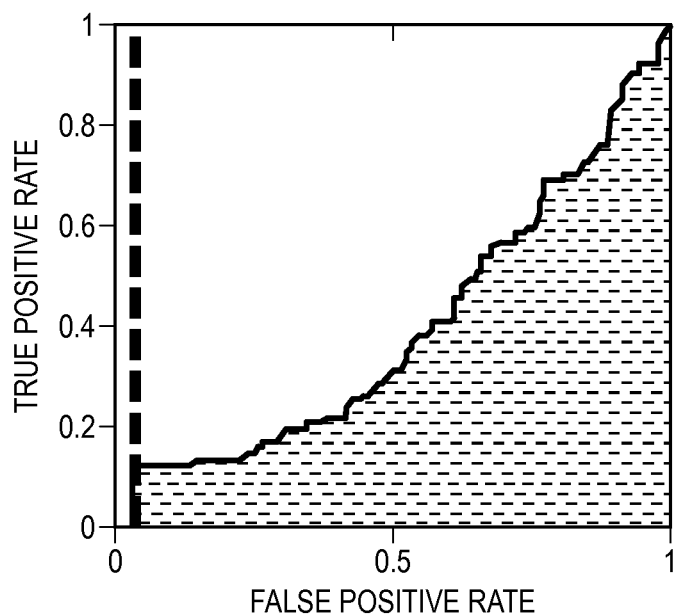
Figure 14B:
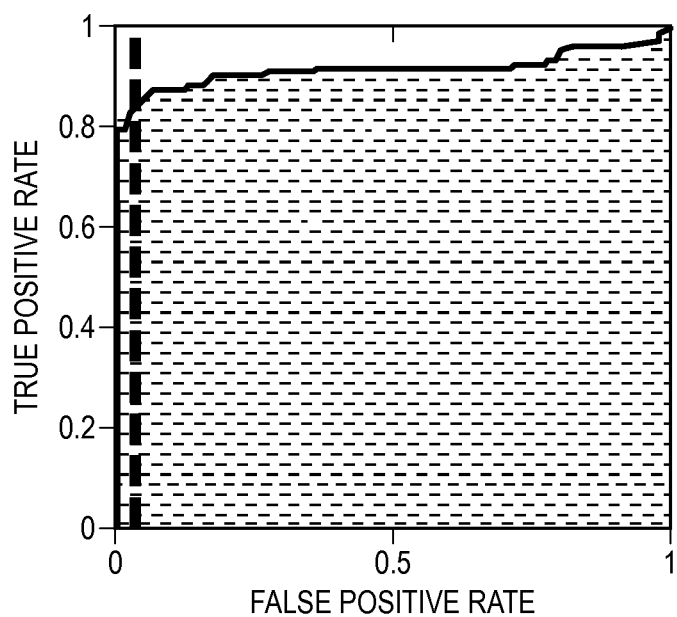
FIG. 14B is a Receiver Operating Characteristic (ROC) curve for the 5 MHz IDP measurements of FIG. 6F.
Figure 15A:
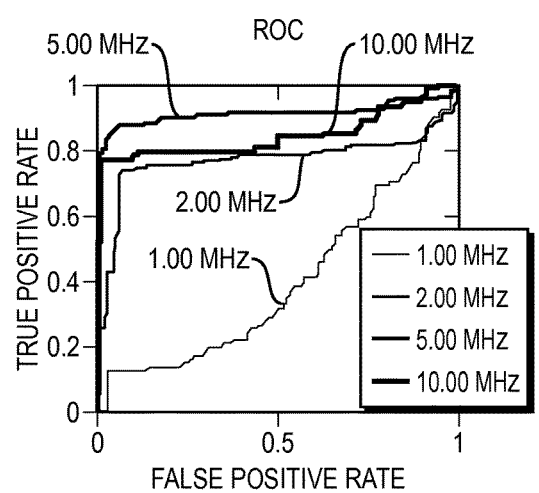
Figure 15B:
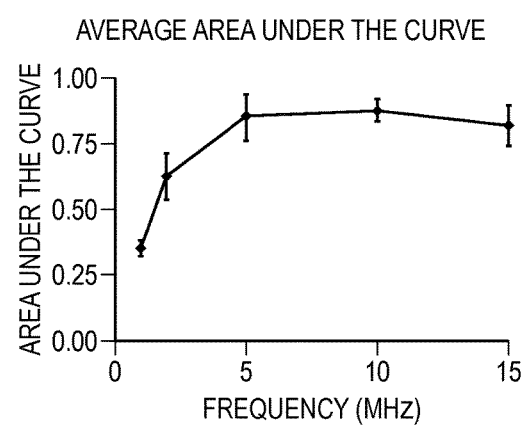
FIG. 15B is a graph of average area under the curve versus frequency.

Further, in accordance with an embodiment of the invention, dielectrophoresis may be used to perform cell manipulation. Generally, electrical properties can encode phenotypic information. AC-electric fields manipulate cells, thereby avoiding electrochemical screening. Cells in a non-uniform electric field will experience a translational force, except when at equilibrium with the surrounding medium. As noted above relative to FIG. 4, in accordance with an embodiment of the invention, cell populations can be characterized and separated based on their iso-dielectric point (IDP) distributions. In addition, as noted above relative to FIG. 6D-6F, activated neutrophils can be filtered from blood at greater than about 5 MHz. In accordance with an embodiment of the invention, isodielectric separation efficiency can be studied using the Area Under the Curve (AUC) of the Receiver Operating Characteristic (ROC) curves. FIG. 14A is a Receiver Operating Characteristic (ROC) curve for the 1 MHz IDP measurements of FIG. 6E, while FIG. 14B is a Receiver Operating Characteristic (ROC) curve for the 5 MHz IDP measurements of FIG. 6F. These curves show the true positive rate versus the false positive rate for the IDP measurements. FIG. 15A is a Receiver Operating Characteristic (ROC) curve for multiple frequencies of IDP measurements, while FIG. 15B is a graph of average area under the curve versus frequency. It can be seen that the ROC curves show a theoretical sorting efficiency of 80-90% using the IDP as a sorting classifier.

Figure 16A:
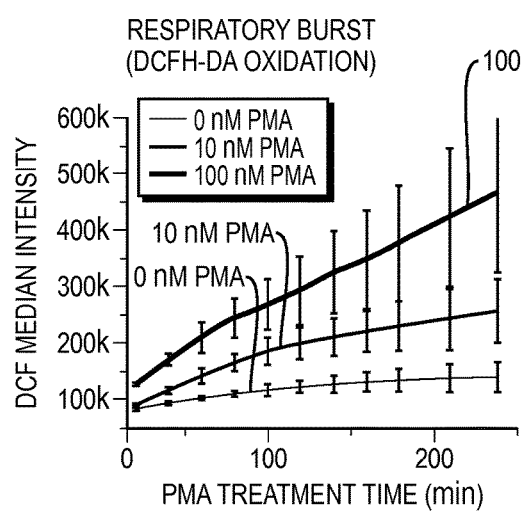
FIG. 16A is a graph of respiratory burst (DCFH-DA oxidation), showing DCF median intensity on the vertical axis, versus PMA (Phorbol 12-Myristate 13-Acetate, Sigma Aldrich) treatment time in minutes (horizontal axis), at different concentrations of PMA.
Figure 16B:
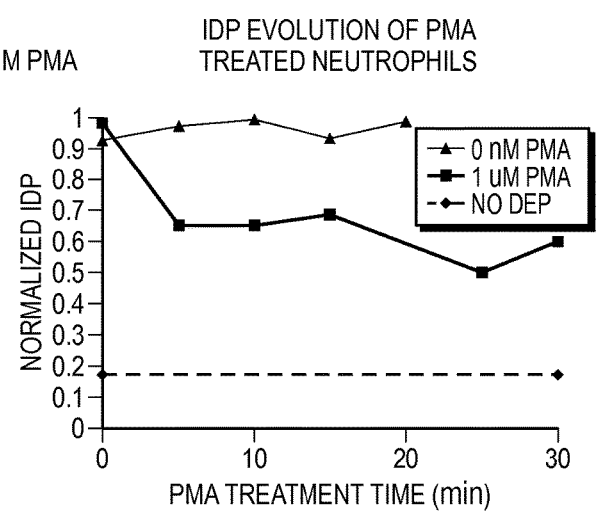
FIG. 16B is a graph of iso-dielectric point (IDP) evolution of PMA-treated neutrophils, showing normalized IDP on the vertical axis versus PMA treatment time in minutes on the horizontal axis.

In another embodiment according to the invention, iso-dielectric position dynamics can be used to assist with diagnostics. In particular, activation of leukocytes can be tracked with DCFH-DA oxidation. FIG. 16A is a graph of respiratory burst (DCFH-DA oxidation), showing DCF median intensity on the vertical axis, versus PMA (Phorbol 12-Myristate 13-Acetate, Sigma Aldrich) treatment time in minutes (horizontal axis), at different concentrations of PMA. FIG. 16B is a graph of iso-dielectric point (IDP) evolution of PMA-treated neutrophils, showing normalized IDP on the vertical axis versus PMA treatment time in minutes on the horizontal axis. It can be seen that IDP changes over time with PMA treatment, which has potential use for diagnostics.

Figure 17A:
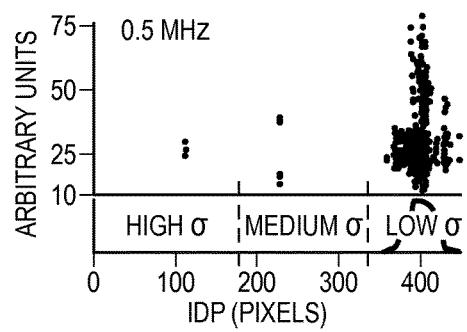
FIGS. 17A-17D are graphs illustrating neutrophil recovery at each of two frequencies, 0.5 MHz in FIGS. 17A and 17B and 10 MHz in FIGS. 17C and 17D.
Figure 17C:
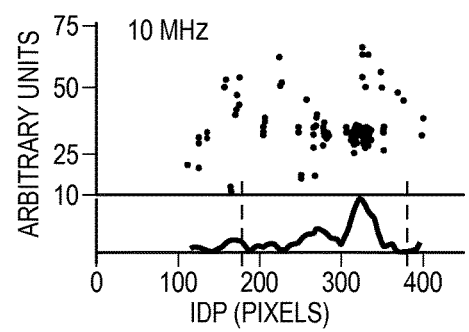
Figure 17B:
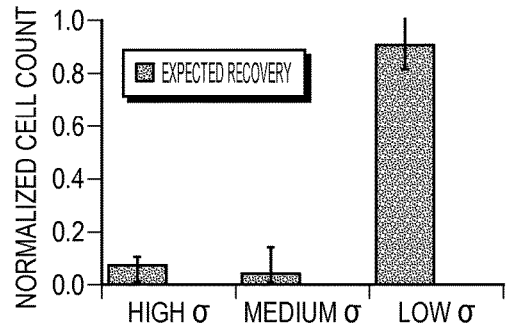
Figure 17D:
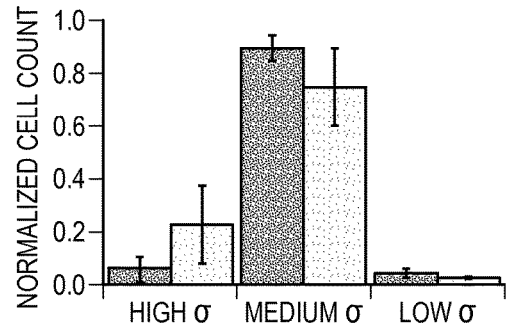

In another embodiment according to the invention, neutrophil recovery can be performed using isodielectric separation, in which nuetrophils can be recovered consistently with their isodielectric position. An integrated system such as that of FIG. 3 can be used, modified in that cells are collected at three outlets of an isodielectric separator 330, in which changing medium conductivity defines three (or another number) of different collection gates. Performance of the sorting results of such a system can be verified by collecting cells, sorted based on IDP characterization, and then verifying the results using flow cytometry. FIGS. 17A-17D are graphs illustrating neutrophil recovery at each of two frequencies, 0.5 MHz in FIGS. 17A and 17B and 10 MHz in FIGS. 17C and 17D. In FIGS. 17A and 17C, IDP in pixels is shown, versus arbitrary units, for high conductivity, medium conductivity and low conductivity media in the IDS separator, at each of the two frequencies. In FIGS. 17B and 17D, the normalized cell counts are shown for each of the high conductivity, medium conductivity and low conductivity media. It can be seen that neutrophils can be recovered consistently with their isodielectric position.

Example 4

Figure 18:
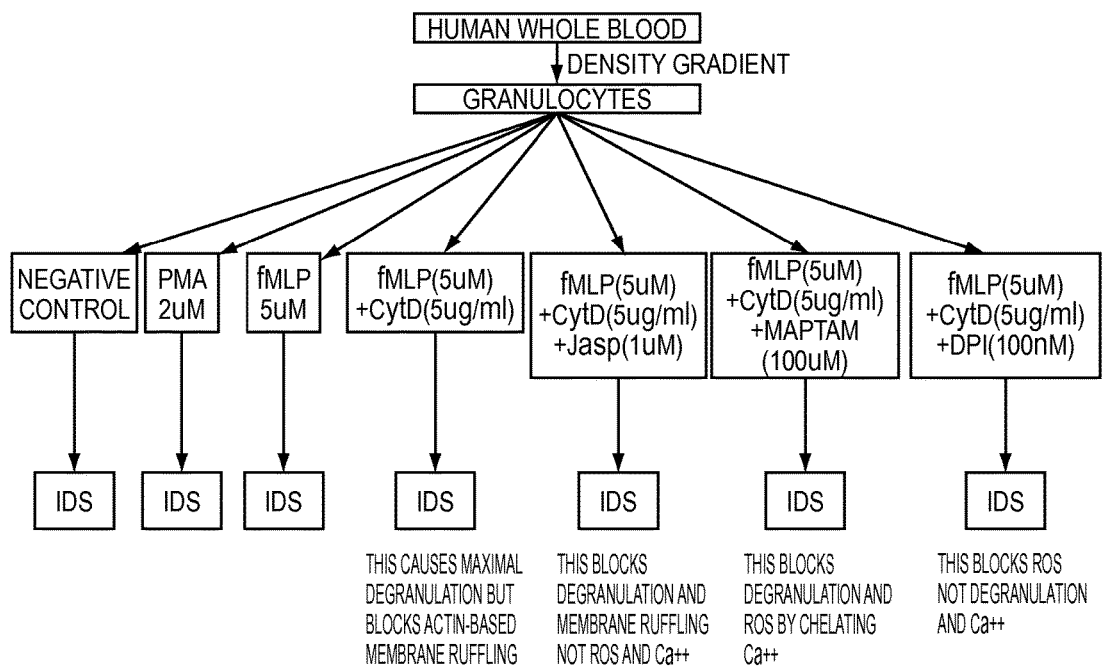
FIG. 18 is a schematic block diagram of the design of a series of experiments to identify, by selectively inhibiting cellular functions, which aspects of the activation signal sequence are linked to the electrical changes utilized for iso-dielectric separation.

Iso-Dielectric Separation Mechanism Study of Neutrophil Activation—Experimental Plan Iso-dielectric separation has shown promising results of high correlation with flow cytometry based activation level, in previous animal experiments. Although the mechanisms underlying the observed electrical changes with cell activation are not currently understood, it is clear that cells undergo changes in intracellular pH with ligand-receptor interactions. It is also plausible that the electrical changes will correlate with cellular functional responses, such as degranulation, oxidative burst, and membrane ruffling. To identify which aspects of the activation signal sequence are linked to the electrical changes utilized for iso-dielectric separation, a series of experiments have been designed to selectively inhibit cellular functions, as shown in the schematic block diagram of FIG. 18. Human whole blood is subjected to a density gradient, and the resulting granulocytes are treated with different drugs to inhibit certain functions. By characterizing the electrical profiles of partially inhibited activated granulocytes, it can be understood what causes the electrical changes of granulocytes during activation.

The experiments utilize the formylated peptide N-Formylmethionyl-leucyl-phenylalanine (fMLP) to activate neutrophils. fMLP is a potent neutrophil chemoattractant that interacts with a family of G-protein coupled formyl peptide receptors (FPR) on neutrophils. fMLP-FPR interactions changes cellular pH and initiates calcium transients to activate intracellular signaling cascades. At higher concentractions, fMLP can also assemble the NADPH oxidase and serve as a neutrophil secretagogue. In addition to fMLP, the experimental plan involves selective use of cytochalasin D (CytD), which is an inhibitor of actin polymerization that increases degranulation and inhibits membrane ruffling. Jasplakinolide (Jasp) is also selectively incorporated into the experimental strategy because this compound is an inducer of actin polymerization, so adding CytD and Jasp will block both degranulation and membrane ruffling. MAPTAM is an intracellular Ca2+ chelator that can block degranulation and reactive oxygen species (ROS) generation by chelating Ca2+. Diphenyleneiodonium chloride (DPI) is an inhibitor of NAPDH oxidase, which blocks the major source for neutrophil reactive oxygen species (ROS) generation. By comparing the difference in electrical profiles under the conditions stated in FIG. 18, the experimental plan aims to identify the mechanism of the electrical changes of activated neutrophils.

Example 5

Iso-Dielectric Separation Mechanism Study of Neutrophil Activation

Figure 19:
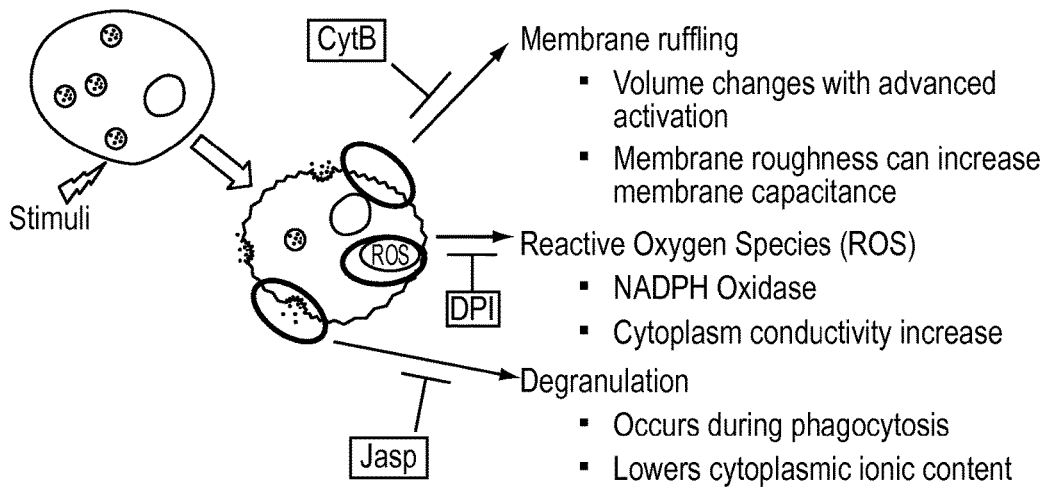
FIG. 19 is a schematic diagram illustrating aspects of activation of a neutrophil in response to a stimulus.
Figure 20A:
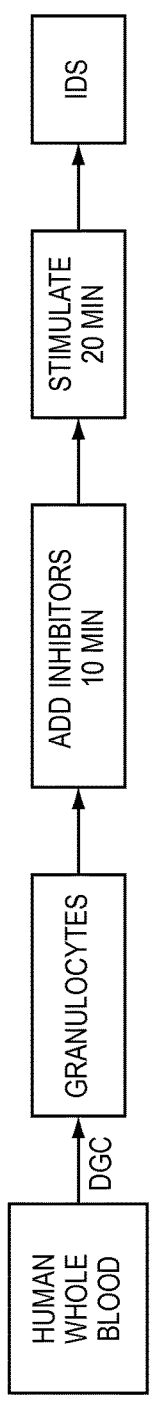
FIG. 20A is a summary of the procedure for an experiment that uses chemical inhibitors to block specific aspects of activation to determine the dominant causes of electrical changes.

This experiment focuses on the mechanism study of electrical changes during neutrophil activation. The mechanism study aims to help understand which aspect of neutrophil activation iso-dielectric separation is sensitive to. Different inhibitors were added to reduce the effect of membrane ruffling, reactive oxygen species (ROS) generation, and degranulation before activation to decouple the effect of the three factors. FIG. 19 is a schematic diagram illustrating aspects of activation of a neutrophil in response to a stimulus. In membrane ruffling, volume changes occur with advanced activation. Membrane roughness can increase the membrane capacitance. In Reactive Oxygen Species (ROS) generation, cytoplasm conductivity increases. NADPH oxidase is a major cause of the ROS generation. Degranulation occurs during phagocytosis, and lowers cytoplasmic ionic content. The experiment uses chemical inhibitors to block specific aspects of activation to determine the dominant causes of electrical changes. FIG. 20A is a summary of the procedure. Human granulocytes are first isolated from whole blood with a density gradient method, and then were split into six aliquots for different treatment. CytB, CytB+Jasp, CytB+DPI were added for inhibiting membrane ruffling, membrane ruffling and degranulation, membrane ruffling and ROS generation, respectively. The inhibition treatment lasted for ten minutes. For activation, the cells were stimulated with fMLP in Ca(+) HBSS buffer for 20 minutes and then loaded into IDS. PMA-treated cells were used as positive control of full activation and non-simulated cells were used as negative control. All the aliquots were treated/stimulated sequentially with ~30 minutes interval.

Figure 20B:
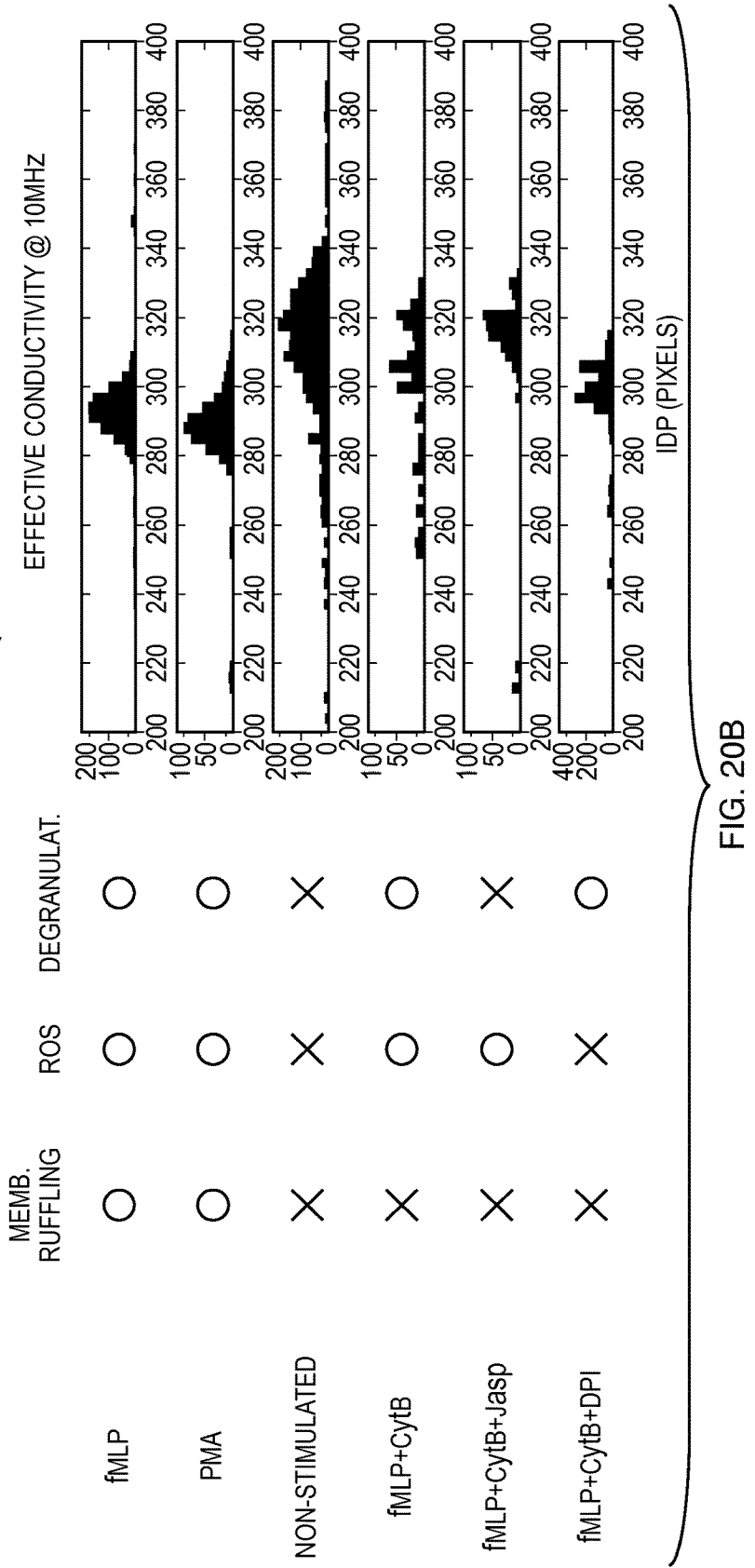
FIG. 20B is a table of the results of the procedure of FIG. 20A. On the right of FIG. 20B are shown the iso-dielectric point (IDP) in pixels, versus arbitrary units, observed for each of the drug treatments listed in corresponding rows on the left of FIG. 20B, thereby illustrating the effective conductivity, at 10 MHz. Also shown in each row of FIG. 20B is the effect of each drug on each of the mechanisms, with an "X" indicating inhibition of a mechanism (membrane ruffling, ROS or degranulation), and an "O" indicating lack of inhibition of the mechanisms.

FIG. 20B shows the results of the procedure of FIG. 20A. On the right of FIG. 20B are shown the iso-dielectric point (IDP) in pixels, versus arbitrary units, observed for each of the drug treatments listed in corresponding rows on the left of FIG. 20B, thereby illustrating the effective conductivity at 10 MHz. Also shown in each row of FIG. 20B is the effect of each drug on each of the mechanisms, with an "X" indicating inhibition of a mechanism (membrane ruffling, ROS or degranulation), and an "O" indicating lack of inhibition of the mechanisms. As expected, the PMA and fMLP stimulated granulocytes (first two rows) shifted to the left, indicating activation. The doses were 0.5 µM for fMLP and 2 µM for PMA, respectively. All the drug-inhibited cases (last four rows) were less left-shifted than the activated control. Among those, CytB+Jasp seems to have most complete inhibition. CytB+DPI is the last sample that we have, the left-shifting could result from natural activation even before the drug was introduced. Based on this initial result, it is speculated that actin-based membrane ruffling can be the main reason of electrical phenotype changes at 10 MHz.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A system comprising:
   a microfluidic device configured to isolate one or more particles from a mixture;
   an electrical measurement device configured to measure an electrical property of the isolated particles; and
   a flow rate matching device configured to match flow rate from the microfluidic device to the flow rate of the electrical measurement device configured to measure an electrical property of the isolated particles.

2. The system of claim 1, wherein the microfluidic device includes at least one spiral channel having a length and a cross-section consisting of a height and a width defining an aspect ratio adapted to isolate particles along portions of the cross-section of the channel based on particle size.

3. The system of claim 2, wherein the aspect ratio of the channel is in a range of between about 2 and about 10.

4. The system of claim 1, wherein the microfluidic device includes a curvilinear microchannel having a trapezoidal cross section defined by a radially inner side, a radially outer side, a bottom side, and a top side, the cross section having the height of the radially inner side smaller than the height of the radially outer side, at a flow rate that isolates particles along portions of the cross-section of the microchannel based on particle size, wherein larger particles flow along the radially inner side of the microchannel to a first outlet and smaller particles flow along other portions of the microchannel to at least one other outlet, thereby size separating the particles from the mixture.

5. The system of claim 1, wherein the flow rate matching device configured to match flow rate is a reservoir for the isolated particles, the reservoir having at least one input for the isolated particles, at least one output for the isolated particles, and a continuous flow of the isolated particles into and out of the reservoir.

6. The system of claim 5, wherein the flow rate of the continuous flow of the isolated particles is in a range of between about 1 ml/min and about 0.0005 ml/min.

7. The system of claim 5, wherein the reservoir includes an injection loop, an excess flow container, or a buffer input.

8. The system of claim 1, wherein the electrical property is the iso-dielectric point.

9. The system of claim 8, wherein the electrical measurement device configured to measure the iso-dielectric point of the isolated particles is an iso-dielectric separation (IDS) device.

10. The system of claim 9, wherein the IDS device is a double-sided IDS device.

11. The system of claim 8, wherein the electrical measurement device configured to measure the iso-dielectric point of the isolated particles is an impedance based electrical properties measurement device.

12. The system of claim 8, wherein the electrical measurement device configured to measure the iso-dielectric point of the isolated particles is a multiple frequency dielectrophoresis device.

13. The system of claim 8, wherein the electrical measurement device configured to measure the iso-dielectric point of the isolated particles is a differential electronic detector of dielectrophoresis translation.

14. The system of claim 1, wherein the electrical property is electrical conductivity.

15. The system of claim 1, wherein the particles are one or more cells.

16. The system of claim 15, wherein the one or more cells are leukocytes.

17. The system of claim 16, wherein the leukocytes are neutrophils.

18. The system of claim 1, wherein the mixture is a biological sample.

19. The system of claim 18, wherein the biological sample is blood.

20. A system comprising:
a microfluidic device configured to isolate one or more particles from a mixture;
an iso-dielectric separation (IDS) device configured to measure an iso-dielectric point of the isolated particles; and
a reservoir configured to match flow rate from the microfluidic device to the flow rate of the IDS device, the reservoir having at least one input for the isolated particles, at least one output for the isolated particles, and a continuous flow of the isolated particles into and out of the reservoir.

21. A method of detecting an inflammatory condition in an individual in need thereof, the method comprising:

a) introducing a sample from the individual comprising one or more white blood cells into a system, wherein the system comprises
(i) a microfluidic device that isolates the one or more white blood cells from the sample,
(ii) an iso-dielectric separation (IDS) device that measures the iso-dielectric point of a cell (IDS device), and
(iii) a reservoir configured to match flow rate from the microfluidic device to the flow rate of the IDS device,
wherein the white blood cells are isolated from the sample in the microfluidic device, then introduced into the reservoir and maintained in the reservoir under conditions in which the flow rate of the one or more isolated white blood cells is matched to the flow rate of the IDS device, then introduced into the IDS device and maintained under conditions in which the iso-dielectric point (IDP) of the white blood cells is measured, and wherein a greater number of cells in the sample having a shift in IDP compared to a control indicates an inflammatory condition.

22. A method of detecting leukocyte activation, the method comprising:
a) introducing a sample comprising leukocytes into a system, wherein the system comprises
(i) a microfluidic device that isolates one or more leukocytes from the sample,
(ii) an iso-dielectric separation (IDS) device that measures the iso-dielectric point of a leukocyte, and
(iii) a reservoir configured to match flow rate from the microfluidic device to the flow rate of the IDS device,
wherein the leukocytes are isolated from the sample in the microfluidic device, then introduced into the reservoir and maintained in the reservoir under conditions in which the flow rate of the one or more isolated leukocytes is matched to the flow rate of the IDS device, then introduced into the IDS device and maintained under conditions in which the iso-dielectric point (IDP) of the leukocytes is measured, wherein a shift in IDP of the leukocytes compared to a control indicates leukocyte activation.

* * * * *